(12) United States Patent
Eagleman et al.

(10) Patent No.: US 11,877,975 B2
(45) Date of Patent: *Jan. 23, 2024

(54) METHOD AND SYSTEM FOR MULTIMODAL STIMULATION

(71) Applicant: NeoSensory, Inc., Palo Alto, CA (US)

(72) Inventors: David M. Eagleman, Palo Alto, CA (US); Michael V. Perrotta, Houston, CA (US)

(73) Assignee: NeoSensory, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/045,141

(22) Filed: Oct. 7, 2022

(65) Prior Publication Data

US 2023/0113744 A1 Apr. 13, 2023

Related U.S. Application Data

(63) Continuation of application No. 17/508,670, filed on Oct. 22, 2021, now Pat. No. 11,497,675.

(Continued)

(51) Int. Cl.
*A61H 23/02* (2006.01)
*A61B 5/00* (2006.01)
(Continued)

(52) U.S. Cl.
CPC ......... *A61H 23/0236* (2013.01); *A61B 5/128* (2013.01); *A61B 5/681* (2013.01);
(Continued)

(58) Field of Classification Search
CPC ....... A61B 5/128; A61B 5/681; A61B 5/7455; H04R 25/75; A61H 23/00–06;
(Continued)

(56) References Cited

U.S. PATENT DOCUMENTS

| 3,342,923 A | 9/1967 | Henley |
| 4,255,801 A | 3/1981 | Ode et al. |

(Continued)

FOREIGN PATENT DOCUMENTS

| CN | 104011794 A | 8/2014 |
| CN | 105739674 A | 7/2016 |

(Continued)

OTHER PUBLICATIONS

"Neosensory Buzz", Neosensory Aug. 17, 2020 (Aug. 17, 2020).

(Continued)

*Primary Examiner* — Valerie L Woodward
*Assistant Examiner* — Paige Kathleen Bugg
(74) *Attorney, Agent, or Firm* — Jeffrey Schox; Caitlin Ploch

(57) ABSTRACT

A system for providing multimodal stimulation to a user includes a tactile device including a set of tactile actuators. Additionally, the system can include and/or interface with a user device, a remote computing system, and/or any other devices. A method for multimodal stimulation functions to provide therapy to a user for tinnitus or other conditions, and includes any or all of: receiving a set of inputs; determining a set of outputs; providing the set of outputs to a user; and adjusting any or all of the set of outputs.

20 Claims, 14 Drawing Sheets

Related U.S. Application Data

(60) Provisional application No. 63/104,944, filed on Oct. 23, 2020, provisional application No. 63/170,961, filed on Apr. 5, 2021.

(51) Int. Cl.
*A61B 5/12* (2006.01)
*A61H 23/00* (2006.01)

(52) U.S. Cl.
CPC ............ *A61B 5/7455* (2013.01); *A61H 23/00* (2013.01); *A61H 2201/165* (2013.01); *A61H 2201/5048* (2013.01)

(58) Field of Classification Search
CPC ........ A61H 2023/002; A61H 2023/045; A61H 2201/165; A61N 1/361; A61N 1/36036
USPC .......................................................... 601/47
See application file for complete search history.

(56) References Cited

U.S. PATENT DOCUMENTS

| | | | |
|---|---|---|---|
| 4,354,064 A | 10/1982 | Scott | |
| 4,581,491 A | 4/1986 | Boothroyd | |
| 4,665,494 A | 5/1987 | Tanaka et al. | |
| 4,926,879 A | 5/1990 | Sevrain et al. | |
| 5,553,148 A | 9/1996 | Werle | |
| 5,655,271 A | 8/1997 | Maxwell-Trumble et al. | |
| 6,027,463 A | 2/2000 | Moriyasu | |
| 6,155,971 A * | 12/2000 | Calhoun | A61F 11/00 |
| | | | 600/549 |
| 6,155,995 A | 12/2000 | Lin | |
| 6,272,466 B1 | 8/2001 | Harada et al. | |
| 6,295,703 B1 | 10/2001 | Adams et al. | |
| 6,671,618 B2 | 12/2003 | Hoisko | |
| 7,146,218 B2 | 12/2006 | Esteller et al. | |
| 7,222,075 B2 | 5/2007 | Petrushin | |
| 7,232,948 B2 | 6/2007 | Zhang | |
| 7,921,069 B2 | 4/2011 | Canny et al. | |
| 7,979,146 B2 | 7/2011 | Ullrich et al. | |
| 8,005,681 B2 | 8/2011 | Hovestadt et al. | |
| 8,068,025 B2 | 11/2011 | Devenyi et al. | |
| 8,588,464 B2 | 11/2013 | Albertson et al. | |
| 8,724,841 B2 | 5/2014 | Bright et al. | |
| 8,754,757 B1 | 6/2014 | Ullrich et al. | |
| 8,952,888 B2 | 2/2015 | Van Den Eerenbeemd et al. | |
| 9,019,087 B2 | 4/2015 | Bakircioglu et al. | |
| 9,064,387 B2 | 6/2015 | Bhatia et al. | |
| 9,104,271 B1 | 8/2015 | Adams et al. | |
| 9,124,979 B2 | 9/2015 | OGrady et al. | |
| 9,147,328 B2 * | 9/2015 | Loffreda | G08B 6/00 |
| 9,298,260 B2 | 3/2016 | Karaoguz et al. | |
| 9,317,116 B2 | 4/2016 | Ullrich et al. | |
| 9,324,320 B1 | 4/2016 | Stolcke et al. | |
| 9,345,433 B1 | 5/2016 | Shinozuka et al. | |
| 9,368,005 B2 | 6/2016 | Cruz-Hernandez et al. | |
| 9,443,410 B1 | 9/2016 | Constien | |
| 9,474,683 B1 | 10/2016 | Mortimer et al. | |
| 9,613,619 B2 | 4/2017 | Lev-Tov et al. | |
| 9,626,845 B2 | 4/2017 | Eagleman et al. | |
| 9,659,384 B2 | 5/2017 | Shaji et al. | |
| 9,682,232 B2 * | 6/2017 | Shore | A61M 21/02 |
| 9,714,075 B2 | 7/2017 | Watkins et al. | |
| 9,735,364 B2 | 8/2017 | Cheng et al. | |
| 9,760,171 B2 | 9/2017 | Cruz-Hernandez et al. | |
| 9,781,392 B2 | 10/2017 | Sahay et al. | |
| 9,905,090 B2 | 2/2018 | Ullrich et al. | |
| 9,987,962 B1 | 6/2018 | Salter et al. | |
| 10,258,790 B2 | 4/2019 | Guarraia et al. | |
| 10,455,320 B2 | 10/2019 | Ralph | |
| 10,497,246 B2 | 12/2019 | Arnold et al. | |
| 10,642,362 B2 | 5/2020 | Eagleman et al. | |
| 10,685,666 B2 | 6/2020 | Maziewski et al. | |
| 10,739,852 B2 | 8/2020 | Amstutz | |
| 11,497,675 B2 * | 11/2022 | Perrotta | A61B 5/7455 |
| 2002/0090100 A1 | 7/2002 | Thiede et al. | |
| 2002/0111737 A1 | 8/2002 | Hoisko | |
| 2002/0194002 A1 | 12/2002 | Petrushin | |
| 2003/0025595 A1 | 2/2003 | Langberg | |
| 2003/0067440 A1 | 4/2003 | Rank | |
| 2003/0117371 A1 | 6/2003 | Roberts et al. | |
| 2003/0151597 A1 | 8/2003 | Roberts et al. | |
| 2003/0158587 A1 | 8/2003 | Esteller et al. | |
| 2003/0179190 A1 | 9/2003 | Franzen | |
| 2005/0113167 A1 | 5/2005 | Buchner et al. | |
| 2005/0192514 A1 * | 9/2005 | Kearby | A61B 5/411 |
| | | | 600/559 |
| 2007/0041600 A1 | 2/2007 | Zachman | |
| 2007/0242040 A1 | 10/2007 | Ullrich et al. | |
| 2008/0120029 A1 | 5/2008 | Zelek et al. | |
| 2008/0140422 A1 | 6/2008 | Hovestadt et al. | |
| 2008/0170118 A1 | 7/2008 | Albertson et al. | |
| 2009/0006363 A1 | 1/2009 | Canny et al. | |
| 2009/0012638 A1 | 1/2009 | Lou | |
| 2009/0096632 A1 | 4/2009 | Ullrich et al. | |
| 2010/0249637 A1 | 9/2010 | Walter et al. | |
| 2010/0302033 A1 | 12/2010 | Devenyi et al. | |
| 2010/0318007 A1 * | 12/2010 | O'Brien | A61H 23/00 |
| | | | 601/48 |
| 2011/0009921 A1 * | 1/2011 | Tass | A61H 1/00 |
| | | | 607/45 |
| 2011/0061017 A1 | 3/2011 | Ullrich et al. | |
| 2011/0063208 A1 | 3/2011 | Van et al. | |
| 2011/0105967 A1 * | 5/2011 | Zeng | A61M 21/00 |
| | | | 607/57 |
| 2011/0202155 A1 | 8/2011 | Ullrich et al. | |
| 2011/0202337 A1 | 8/2011 | Fuchs et al. | |
| 2011/0221694 A1 | 9/2011 | Karaoguz et al. | |
| 2011/0319796 A1 | 12/2011 | Campdera | |
| 2012/0023785 A1 | 2/2012 | Barnes et al. | |
| 2012/0046579 A1 * | 2/2012 | Radl | A61H 11/00 |
| | | | 601/46 |
| 2012/0283593 A1 * | 11/2012 | Searchfield | H04R 25/75 |
| | | | 381/17 |
| 2013/0102937 A1 | 4/2013 | Ehrenreich et al. | |
| 2013/0163797 A1 * | 6/2013 | Suzman | H04R 25/75 |
| | | | 381/314 |
| 2013/0218456 A1 | 8/2013 | Zelek et al. | |
| 2013/0265286 A1 | 10/2013 | Da Costa et al. | |
| 2014/0064516 A1 | 3/2014 | Cruz-Hernandez et al. | |
| 2014/0176415 A1 | 6/2014 | Buuck et al. | |
| 2014/0270190 A1 | 9/2014 | Flynn et al. | |
| 2014/0350441 A1 * | 11/2014 | Shafieloo | A61H 23/0263 |
| | | | 601/48 |
| 2014/0363138 A1 | 12/2014 | Coviello et al. | |
| 2015/0003635 A1 * | 1/2015 | Baker | H04R 25/50 |
| | | | 381/104 |
| 2015/0025895 A1 | 1/2015 | Schildbach | |
| 2015/0038887 A1 | 2/2015 | Piccirillo | |
| 2015/0070150 A1 | 3/2015 | Levesque et al. | |
| 2015/0120289 A1 | 4/2015 | Lev-Tov et al. | |
| 2015/0126802 A1 * | 5/2015 | Lim | A61N 1/36082 |
| | | | 607/45 |
| 2015/0161994 A1 | 6/2015 | Tang et al. | |
| 2015/0161995 A1 | 6/2015 | Sainath et al. | |
| 2015/0227204 A1 | 8/2015 | Gipson et al. | |
| 2015/0230524 A1 | 8/2015 | Stevens et al. | |
| 2015/0241975 A1 | 8/2015 | Bhatia et al. | |
| 2015/0272815 A1 | 10/2015 | Kitchens | |
| 2015/0294597 A1 | 10/2015 | Rizzo | |
| 2015/0305974 A1 | 10/2015 | Ehrenreich et al. | |
| 2015/0351999 A1 | 12/2015 | Brouse | |
| 2015/0356889 A1 | 12/2015 | Schwartz | |
| 2016/0012688 A1 | 1/2016 | Eagleman et al. | |
| 2016/0026253 A1 | 1/2016 | Bradski et al. | |
| 2016/0027338 A1 | 1/2016 | Ebeling et al. | |
| 2016/0049915 A1 | 2/2016 | Wang et al. | |
| 2016/0098844 A1 | 4/2016 | Shaji et al. | |
| 2016/0098987 A1 | 4/2016 | Stolcke et al. | |
| 2016/0103590 A1 | 4/2016 | Vu et al. | |
| 2016/0187987 A1 | 6/2016 | Ullrich et al. | |
| 2016/0254454 A1 | 9/2016 | Cheng et al. | |

(56) References Cited

U.S. PATENT DOCUMENTS

| | | |
|---|---|---|
| 2016/0255944 A1 | 9/2016 | Baranski et al. |
| 2016/0284189 A1 | 9/2016 | Constien |
| 2016/0292856 A1 | 10/2016 | Niemeijer et al. |
| 2016/0297611 A1 | 10/2016 | Williams et al. |
| 2016/0358429 A1 | 12/2016 | Ullrich et al. |
| 2016/0367190 A1 | 12/2016 | Vaitaitis |
| 2017/0169673 A1 | 6/2017 | Billington et al. |
| 2017/0206889 A1 | 7/2017 | Lev-Tov et al. |
| 2017/0213568 A1 | 7/2017 | Foshee |
| 2017/0290736 A1 | 10/2017 | Idris |
| 2017/0294086 A1 | 10/2017 | Kerdemelidis |
| 2017/0348184 A1 | 12/2017 | Pisharodi et al. |
| 2018/0033263 A1 | 2/2018 | Novich et al. |
| 2018/0210552 A1 | 7/2018 | Saboune et al. |
| 2018/0284894 A1 | 10/2018 | Raut et al. |
| 2018/0303702 A1* | 10/2018 | Novich .................. G06V 20/20 |
| 2018/0315343 A1 | 11/2018 | Shvartzberg et al. |
| 2018/0374264 A1 | 12/2018 | Gatson et al. |
| 2019/0045296 A1 | 2/2019 | Ralph |
| 2019/0201657 A1* | 7/2019 | Popelka .................. H04R 25/75 |
| 2019/0337451 A1 | 11/2019 | Bacchus et al. |
| 2019/0379977 A1 | 12/2019 | Buttner et al. |
| 2020/0121544 A1* | 4/2020 | George .................... A61H 9/00 |
| 2020/0209975 A1 | 7/2020 | Eagleman et al. |
| 2021/0089130 A1 | 3/2021 | Novich et al. |
| 2021/0110841 A1 | 4/2021 | Weber et al. |
| 2021/0169735 A1* | 6/2021 | Northen ................. A61H 1/005 |
| 2021/0325969 A1 | 10/2021 | Eagleman et al. |
| 2022/0023137 A1* | 1/2022 | Rha ........................ G10K 15/02 |
| 2022/0078566 A1 | 3/2022 | Haefeli |

FOREIGN PATENT DOCUMENTS

| | | | |
|---|---|---|---|
| EP | 0911002 A2 | 4/1999 | |
| WO | 2008106698 A1 | 9/2008 | |
| WO | 2012069429 A1 | 5/2012 | |
| WO | 2015028480 A1 | 3/2015 | |
| WO | WO-2015028480 A1 * | 3/2015 | ............. H04R 25/75 |

OTHER PUBLICATIONS

"The Wristband That Gives You Superpowers", NEO.LIFE, Jan. 10, 2019 (Jan. 10, 2019) 1-16.

Conlon, Brendan, et al., "Biomodal neuromodulation combining sound and tongue stimulation reduces tinnitus symptoms in a large randomized clinical study", Science Translational Medicine, Research Article, 12, eabb2830 (2020) Oct. 7, 2020.

Graves, Alex, et al., "Bidirectional LSTM Networks for Improved Phoneme Classification and Recognition", ResearchGate, Conference Paper, Jan. 2005.

Horvath, Samantha, et al., "FingerSight: Fingertip Haptic Sensing of the Visual Environment", Mar. 6, 2014, IEEE, vol. 2, 2014 (Year: 2014).

Naguma, Hirofumi, et al., "Minimum Latency Training Strategies for Streaming Sequence-To-Sequence ASR", arXiv:2004.05009v2, May 15, 2020, Accepted at IEEE ICASSP 2020.

Jones, Lynette A., et al., "Development of a Tactile Vest", 2004, IEEE, 0-7695-2112-6/04 (Year: 2004).

Nakamura, Mealani, et al., "An Actuator for the Tactile Vest—a Torso-Based Haptic Device", 2003, IEEE, 0-7695-1890-7/03 (Year: 2003).

Paneels, Sabrina, et al., "What's Around Me? Multi-Actuator Haptic Feedback on the Wrist", Apr. 14-18, 2013, IEEE, 978-1-4799-0088-6/13, pp. 407-412 (Year: 2013).

Plant, Geoff, "Training in the use of the Tactaid VII: A case study", KTH Computer Science and Communication (STL-QPSR), 1994, vol. 35, No. 1, pp. 091-102., Jul. 24, 2017 00:00:00.0.

Tapson, Jonathan, et al., "The Feeling of Color: A Haptic Feedback Device for the Visually Disabled", 2008, IEEE, 978-1-4244-2879-3/08, pp. 381-384 (Year: 2008).

Yu, Haibao, et al., "Low-bit Quantization Needs Good Distribution", Published in: 2020 IEEE/CVF Conference on Computer Vision and Pattern Recognition Workshops (CVPRW), Jun. 14-19, 2020.

* cited by examiner

Tactile device set of actuators

| Tone frequency of audio output at speaker (Ordering of tones optionally determined with a randomization process) | Amplitudes of x actuators at tactile device to product tactile output | Time at which audio output and tactile output is applied | Temporal delay values optionally determined with a randomization process |
|---|---|---|---|
| $f_4$ | $(A_{1,1}, A_{2,1}, A_{3,1}, \ldots A_{x,1})$ | $t_1$ | $\Delta t_1$ |
| $f_{n-1}$ | $(A_{1,2}, A_{2,2}, A_{3,2}, \ldots A_{x,2})$ | $t_2$ | $\Delta t_2$ |
| $f_2$ | $(A_{1,3}, A_{2,3}, A_{3,3}, \ldots A_{x,3})$ | $t_3$ | $\Delta t_3$ |
| $f_n$ | $(A_{1,4}, A_{2,4}, A_{3,4}, \ldots A_{x,4})$ | $t_4$ | |
| ... | ... | ... | |
| $f_{n-2}$ | $(A_{1,n-3}, A_{2,n-3}, A_{3,n-3}, \ldots A_{x,n-3})$ | $t_{n-3}$ | $\Delta t_{n-3}$ |
| $f_3$ | $(A_{1,n-2}, A_{2,n-2}, A_{3,n-2}, \ldots A_{x,n-2})$ | $t_{n-2}$ | $\Delta t_{n-2}$ |
| $f_{n-3}$ | $(A_{1,n-1}, A_{2,n-1}, A_{3,n-1}, \ldots A_{x,n-1})$ | $t_{n-1}$ | $\Delta t_{n-1}$ |
| $f_1$ | $(A_{1,n}, A_{2,n}, A_{3,n}, \ldots A_{x,n})$ | $t_n$ | $\Delta t_n$ |
| $f_3$ | $(A_{1,n+1}, A_{2,n+1}, A_{3,n+1}, \ldots A_{x,n+1})$ | $t_{n+1}$ | $\Delta t_{n+1}$ |
| $f_{n-3}$ | $(A_{1,n+2}, A_{2,n+2}, A_{3,n+2}, \ldots A_{x,n+2})$ | $t_{n+2}$ | $\Delta t_{n+2}$ |
| $f_2$ | $(A_{1,n+3}, A_{2,n+3}, A_{3,n+3}, \ldots A_{x,n+3})$ | $t_{n+3}$ | $\Delta t_{n+3}$ |
| $f_{n-1}$ | $(A_{1,n+4}, A_{2,n+4}, A_{3,n+4}, \ldots A_{x,n+4})$ | $t_{n+4}$ | |
| ... | ... | ... | |
| $f_n$ | $(A_{1,2n-3}, A_{2,2n-3}, A_{3,2n-3}, \ldots A_{x,2n-3})$ | $t_{2n-3}$ | $\Delta t_{2n-3}$ |
| $f_{n-2}$ | $(A_{1,2n-2}, A_{2,2n-2}, A_{3,2n-2}, \ldots A_{x,2n-2})$ | $t_{2n-2}$ | $\Delta t_{2n-2}$ |
| $f_4$ | $(A_{1,2n-1}, A_{2,2n-1}, A_{3,2n-1}, \ldots A_{x,2n-1})$ | $t_{2n-1}$ | $\Delta t_{2n-1}$ |
| $f_1$ | $(A_{1,2n}, A_{2,2n}, A_{3,2n}, \ldots A_{x,2n})$ | $t_{2n}$ | |

FIGURE 9B

METHOD AND SYSTEM FOR MULTIMODAL STIMULATION

CROSS-REFERENCE TO RELATED APPLICATIONS

This application is a continuation of U.S. application Ser. No. 17/508,670, filed 22 Oct. 2021, which claims the benefit of US Provisional Application No. 63/170,961, filed 5 Apr. 2021, and US Provisional Application No. 63/104,944, filed 23 Oct. 2020, each of which is incorporated in its entirety by this reference.

TECHNICAL FIELD

This invention relates generally to the sensory output and signals processing fields, and more specifically to a new and useful system and method for providing multimodal stimulation in the sensory output and signals processing fields.

BACKGROUND

Tinnitus is a phantom auditory perception, which causes a disruptive "ringing in the ear" sensation to individuals experiencing it, which can be extremely debilitating. There are currently no cures for this condition, and conventional systems and methods which attempt to mitigate these symptoms are invasive and/or obstructive, requiring for instance, that users apply electrical stimulation to the scalp or tongue in an attempt to apply current which activates nerves of the peripheral nervous system, or other particular areas of the brain.

The inventors have discovered that haptic stimulation provided to various locations of the user's body (e.g., wrist) in addition to other forms of stimulation, such as audio, can be extremely effective in improving particular auditory conditions, including tinnitus, without being obstructive, inconvenient, uncomfortable, or otherwise interfering with the daily activities of users. The system and method below describe this invention.

BRIEF DESCRIPTION OF THE FIGURES

FIGS. 9A-9D depict an example or providing multimodal stimulation to a user.

DESCRIPTION OF THE PREFERRED EMBODIMENTS

The following description of the preferred embodiments of the invention is not intended to limit the invention to these preferred embodiments, but rather to enable any person skilled in the art to make and use this invention.

1. Overview

Figure 1:
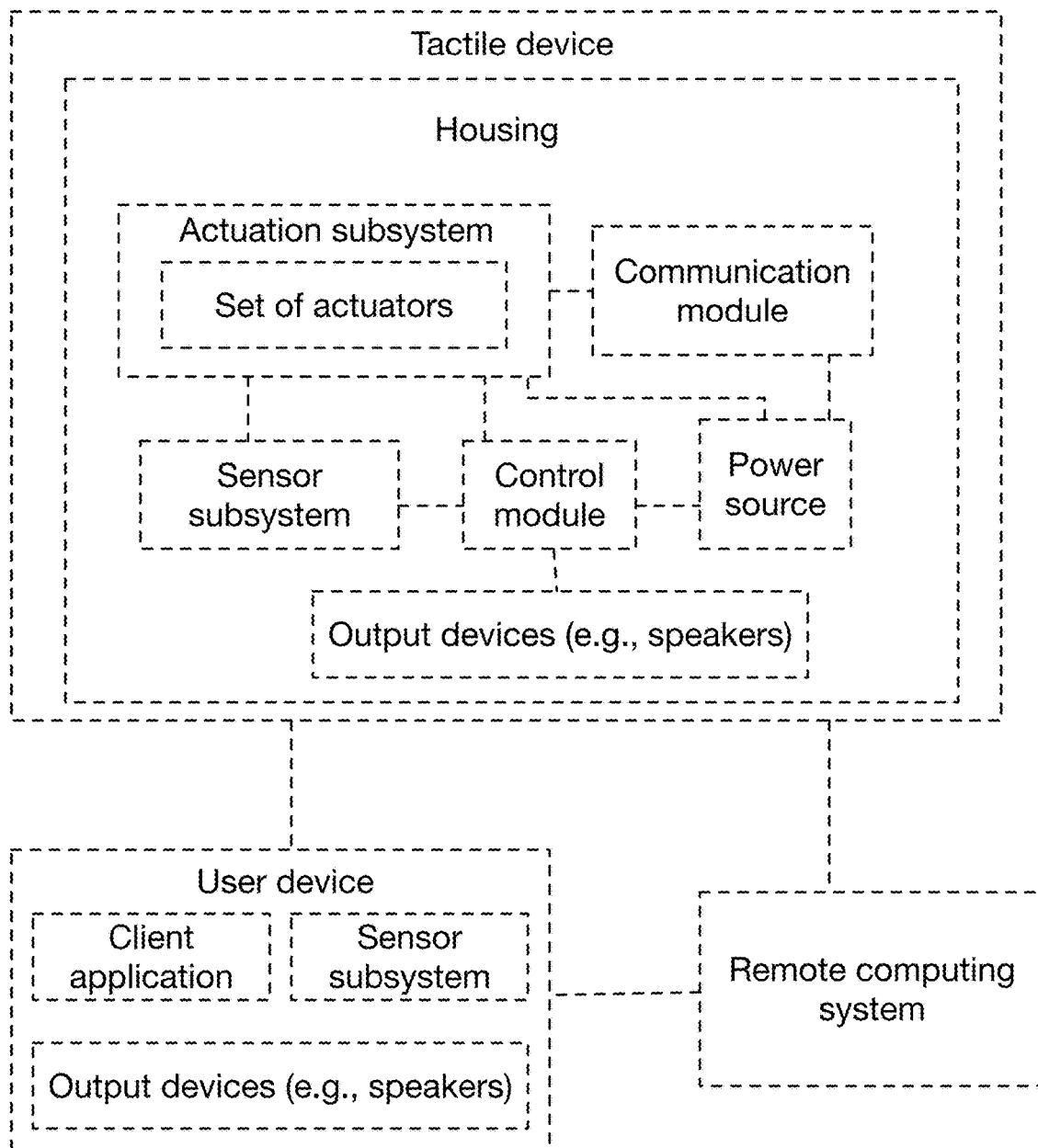
FIG. 1 is a schematic of a system for multimodal stimulation.

As shown in FIG. 1, a system 100 for multimodal stimulation includes a tactile device. Additionally or alternatively, the system 100 can include and/or interface with any or all of the systems, components, embodiments, and/or examples described in any or all of: U.S. Application Ser. No. 17/033,433, filed 25 Sep. 2020, and U.S. Application Ser. No. 17/144,076, filed 7 Jan. 2021, each of which is incorporated in its entirety by this reference.

The system 100 is preferably configured to perform any or all of method 200 as described below, but can additionally or alternatively be used to perform any other method(s).

Figure 2:
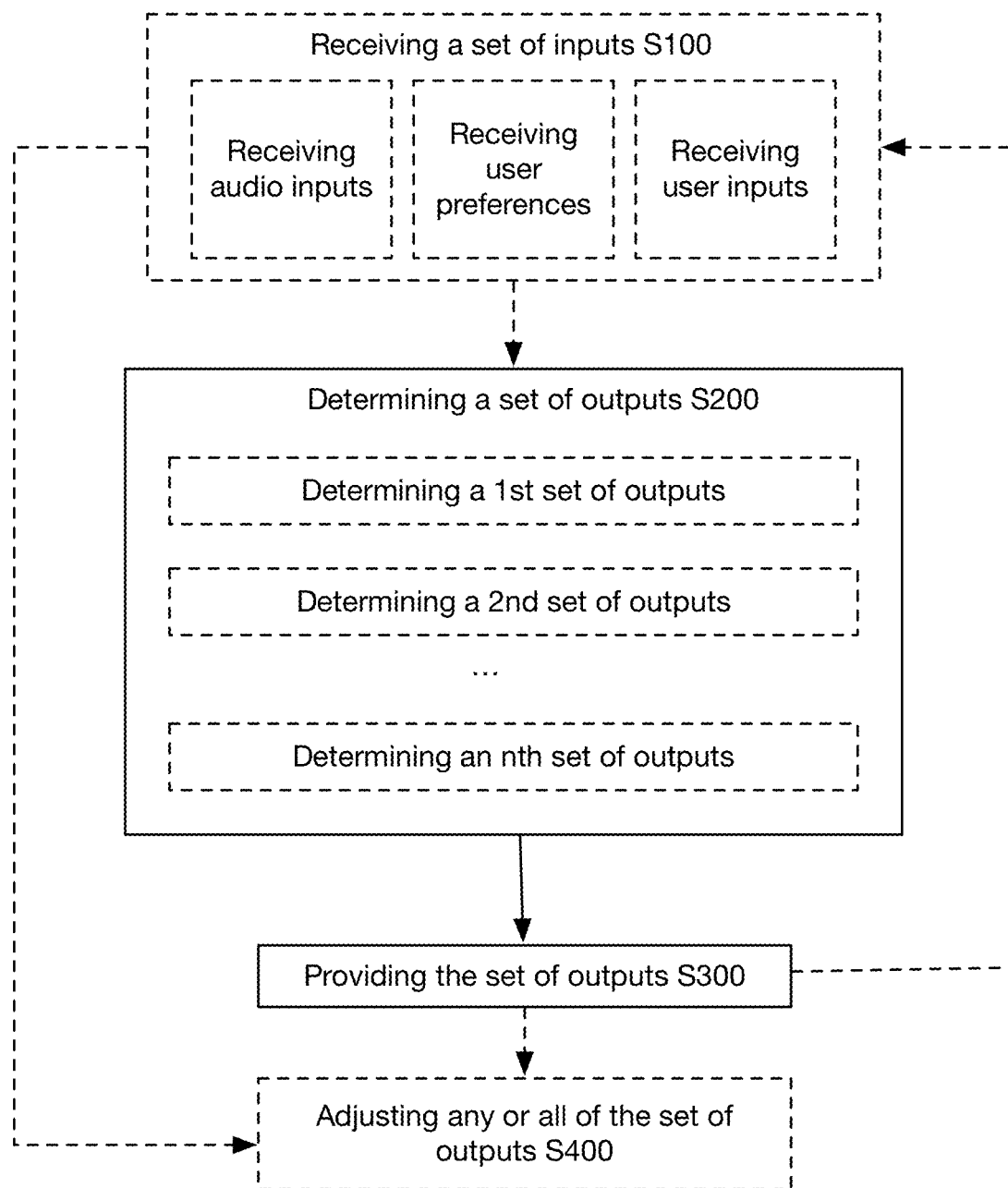
FIG. 2 is a schematic of a method for multimodal stimulation.

As shown in FIG. 2, a method 200 for multimodal stimulation includes determining a set of outputs S200 and providing the set of outputs S300. Additionally or alternatively, the method 200 can include receiving a set of inputs S100, adjusting any or all of the set of outputs S400, and/or any other suitable processes. Further additionally or alternatively, the method 200 can include and/or interface with any or all of the methods, processes, embodiments, and/or examples described in any or all of: U.S. Application Ser. No. 17/033,433, filed 25 Sep. 2020, and U.S. application Ser. No. 17/144,076, filed 7 Jan. 2021, each of which is incorporated in its entirety by this reference, or any other suitable processes performed in any suitable order.

The method 200 can be performed with a system as described above and/or any other suitable system.

2. Benefits

The system and method for multimodal stimulation can confer several benefits over current systems and methods.

In a first variation, the system and/or method confers the benefit of minimizing, alleviating, and/or preventing the occurrence of tinnitus through multimodal stimulation provided with a non-invasive and un-obstructive wearable device (e.g., wristband, vest, arm band, headband, etc.), such as one which provides tactile stimulation at a skin surface of the user (e.g., rather than exciting a peripheral nerve at the tongue and/or other head region of the user). This can further confer the benefits of any or all of: providing portable tinnitus therapy, enabling a user to perform tasks or be otherwise uninhibited while receiving tinnitus therapy (e.g., talk without having a device placed on the tongue, eat, etc.), providing comfortable tinnitus therapy, providing safe tinnitus therapy, and/or can confer any other benefits.

In a first set of examples, the system and/or method confer the benefit of minimizing, alleviating, and/or preventing the occurrence of tinnitus by implementing tone-based therapy (or therapy with other types of audio) through bimodal stimulation including haptic stimulation and audio stimulation with a haptic device. In a specific example, a set of tones are played for the user with a speaker while a corresponding set of tactile outputs (e.g., vibrations) are provided to a skin surface of the user.

In a second set of examples, the system and/or method implement organic exposure therapy with bimodal stimulation including haptic stimulation provided at a tactile device in response to detection of sounds naturally occurring in the user's environment.

In additional or alternative variations, the system and/or method can confer the benefit of alleviating any other conditions (e.g., auditory conditions, neurological conditions, sensory conditions, etc.) of the user through one or more stimulation (e.g., unimodal, bimodal, trimodal, greater than trimodal, etc.) protocols.

In a second variation, additional or alternative to the first, the system and/or method confer the benefit of expanding a range of locations at which tactile stimulation can be perceived by user through the implementation of one or more illusion-based tactile effects (equivalently referred to herein as phantom sensation). This can, in turn, function to minimize a number of motors required to be onboard a tactile stimulation device worn by the user, enable stimulation to be perceived at a large and continuous range of locations (e.g., which represent/are mapped in the user's brain to a large and continuous range of frequencies), enable users with varying types of tinnitus (e.g., tinnitus associated with different frequency values) to use the same device, and/or confer any other benefits. In a set of specific examples, for instance, the system provides tactile sensation in accordance with a funneling tactile illusion in which the contemporaneous (e.g., simultaneous, overlapping, at least partially overlapping, etc.) stimulation of two motors (e.g., with different amplitudes) produces a perceived sensation at a virtual location between the motors (e.g., and located closer to the motor associated with the higher amplitude). Additionally or alternatively, the motors can be operated in accordance with other tactile illusions (e.g., saltation, cutaneous rabbit, etc.), in absence of a tactile illusion, and/or otherwise operated.

In a third variation, additional or alternative to those described above, the system and/or method confers the benefit of monitoring the progression of a tinnitus condition of a user and adapting his or her bimodal stimulation based on how it is progressing. In specific examples, user input at an interactive client application is analyzed and monitored to adapt the user's bimodal stimulation plan accordingly (e.g., by adjusting a frequency of the audio outputs played for the user, by adjusting a loudness of the audio outputs played for the user, by adjusting locations of the tactile stimulation provided to the user, by adjusting a duration of the bimodal stimulation plan, by adjusting a recommended frequency with which the user participates in the bimodal stimulation plan, etc.).

In a fourth variation, additional or alternative to those described above, the system and/or method confers the benefit of using learnings from a first user to optimize (e.g., determine, select, and/or adjust) the bimodal stimulation plan of a second user. In specific examples, for instance, a second user can be assigned to the first user's subgroup (of a set of multiple user subgroups) based on shared characteristics between the second user and the first user (e.g., shared tinnitus frequency value, shared tinnitus loudness value, etc.), where the bimodal stimulation plan for the second user is determined based on the particular subgroup (e.g., shared among all users of that subgroup).

Additionally or alternatively, the system and method can confer any other benefit.

3. System 100

As shown in FIG. 1, a system 100 for multimodal stimulation includes a tactile device. Additionally or alternatively, the system 100 can include and/or interface with any or all of the systems, components, embodiments, and/or examples described in any or all of: U.S. Application Ser. No. 17/033,433, filed 25 Sep. 2020, and U.S. Application Ser. No. 17/144,076, filed 7 Jan. 2021, each of which is incorporated in its entirety by this reference.

The system 100 preferably functions to provide multimodal stimulation (e.g., bimodal, trimodal, etc.) to a user, wherein the multimodal stimulation includes haptic stimulation and optionally any or all of: audio stimulation, optical stimulation, olfactory stimulation, gustatory stimulation, and/or any other forms of stimulation. This multimodal stimulation preferably subsequently functions to implement a therapy protocol for an auditory condition (e.g., tinnitus, hearing loss, etc.), but can additionally or alternatively be implemented in accordance with other conditions and/or in absence of a condition.

The system 100 includes a tactile device (equivalently referred to herein as a haptic device), wherein the tactile device functions to provide tactile stimulation to a user. The tactile device is preferably a wearable device configured to be reversibly coupled (e.g., with a fastener, garment, etc.) to the user, but can additionally or alternatively include a device irreversibly coupled to the user. Further additionally or alternatively, the tactile device can be a non-wearable device such as a tabletop device, handheld device, and/or any other suitable device.

The tactile device includes an actuation subsystem, which functions to apply the haptic (e.g., vibratory) stimulation to the user. The actuation subsystem includes a set of actuators (e.g., motors, vibratory motors, etc.), which individually and/or collectively function to provide the haptic stimulation to a body region of the user. In a preferred set of variations, the body region includes a partial or full circumference of one or more wrists of the user, but can additionally or alternatively include any or all of: a hand, arm, finger, leg, torso, neck, head, ankle, and/or any other suitable body part or body region of the user.

The set of actuators can include one or more of: a motor (e.g., brushless motor, brushed motor, direct current (DC) motor, alternating current (AC) motor, eccentric rotating mass (ERM), etc.), an actuator (e.g., linear resonant actuator (LRA), electroactive polymer (EAP) actuator, electromechanical polymer (EMP) actuator, etc.), a piezoelectric device, and/or any other form of vibratory element. In a set of actuators including multiple actuators, the actuators can be arranged in an array (e.g., 1-dimensional array, 2-dimensional array, 3-dimensional array, etc.), arranged at least partially circumferentially around the body part (e.g., around a wrist, around half of the circumference of the wrist, etc.), arranged along the body part (e.g., up and down an arm), arranged over a body region (e.g., over the user's trunk, stomach, etc.), arranged among different body parts of a user (e.g., arranged around both wrists), and/or arranged in any other suitable way. The vibratory elements can be directly coupled to the skin of a user, separated from a user by an element of the housing (e.g., the wristband), placed over a user's clothing, and/or coupled to the user in any other way. In variations of the system configured to apply haptic stimulation to a wrist or other limb of the user, the system preferably includes 4 LRA actuators arranged around a portion of the circumference (e.g., half the circumference) of the wrist. Additionally or alternatively, the system can include actuators circumscribing the entire wrist (e.g., 8 LRA actuators), and/or any other suitable number and arrangement of actuators.

The actuation subsystem is preferably operated in accordance with a set of stimulation patterns (e.g., series of stimulation patterns), wherein the stimulation patterns prescribe any or all of the following to the set of actuators (e.g., individually, collectively, etc.): amplitude of vibration, timing of vibration (e.g., when to start, duration, when to end, duration of time between vibrations, etc.), sequence of vibration, identification of which of the set of actuators to vibrate, frequency of vibration, and/or any other parameter(s) of stimulation. In preferred variations, the stimulation pattern prescribes an amplitude of vibration and a duration of vibration to one or more actuators of the set of actuators, wherein each of the set of actuators is configured to vibrate at a fixed frequency. Additionally or alternatively, the stimulation pattern can prescribe a frequency of vibration, a dynamic pattern of vibration (e.g., alternating between actuators), and/or any other suitable characteristic or parameter(s) of vibration.

Additionally or alternatively, the actuation subsystem can be operable in any number of modes, wherein the method 200, for instance, can be performed in accordance with a particular operation mode. Additionally or alternatively, the tactile device can be otherwise operated.

In variations involving tinnitus therapy, the tactile stimulation pattern(s) (equivalently referred to herein as stimulation patterns) are preferably determined in accordance with a set of audio outputs to be conveyed to the user, such as a set of audio tones (e.g., predetermined audio tones, dynamically determined audio tones, etc.) provided as a tone-based audio therapy. Additionally or alternatively, the stimulation pattern(s) can be determined based on other information (e.g., other audio, other types of information, etc.), determined based on user preferences (e.g., for selecting parameters), determined independently of other information, and/or otherwise determined. Further additionally or alternatively, the audio therapy can include audio other than audio tones and/or any combination of audio.

The stimulation pattern(s) can additionally or alternatively function to convey information, such as any or all of: speech (e.g., such that the user can engage in conversation), music (e.g., composition of the music, "feel" of the music, etc.), environmental sounds (e.g., nature sounds, crosswalk indicator sounds, alarm clock, phone ring, phone notification, vehicle driving, etc.), safety sounds and/or alarms (e.g., smoke alarm, siren, vehicle horn, etc.), and/or any other suitable sounds.

The actuation subsystem can include a haptic driver (e.g., LRA driver) configured to actuate the set of actuators according to the stimulation pattern. Additionally or alternatively, the actuators can be actuated in any suitable way with any other suitable component(s).

The system can additionally include a housing, which functions to support the set of actuators. The housing can additionally or alternatively function to: suspend the set of actuators, maintain a separation distance between the set of actuators, maintain an offset (e.g., minimize, maintain a constant offset, etc.) of the set of actuators from a skin surface of the user, conform to a variety of users (e.g., conform to a variety of user wrist sizes, flex to wrap around a user's wrist, etc.), house other components of the system (e.g., sensor subsystem, control module, etc.), be comfortable to a user, enhance a vibration of the actuators (e.g., minimize a dampening of the haptic output), reduce direct sound transmission from the set of actuators to a microphone, maintain an orientation of the system on a user (e.g., prevent rotation of the support subsystem on the wrist of a user), assist in alignment of the support subsystem, and/or perform any other suitable function.

The system can optionally include a sensor subsystem, which can function to determine information in an environment of the user. This can include, for instance, audio information from a set of microphones (e.g., unidirectional microphones, bidirectional microphones, omnidirectional microphones, etc.) or other audio sensors with which to determine and/or trigger haptic stimulation to be applied to the user (e.g., in organic exposure therapy for tinnitus). Additionally or alternatively, the sensor subsystem can include any other suitable sensors (e.g., camera or other optical sensor(s), GPS system or other location sensor(s), accelerometer and/or gyroscope and/or other motion sensor(s), etc.) configured to perform any other suitable function(s).

The sensor subsystem can be arranged onboard the tactile device, offboard the tactile device (e.g., remote from the tactile device, onboard a user device in communication with the tactile device, in an environment of the user, etc.), or any combination.

The system can optionally include any number of output devices, such as, but not limited to, any or all of: speakers (e.g., to provide audio outputs), optical components (e.g., lights, light emitting diodes [LEDs], etc.), and/or any other output devices.

The output devices can be arranged onboard the tactile device, offboard the tactile device (e.g., remote from the tactile device, onboard a user device in communication with the tactile device, in an environment of the user, etc.), or any combination. In specific examples, for instance, the speakers of a user device in communication with the tactile device are used to provide audio outputs as part of an audio (e.g., tone) therapy protocol. In additional or alternative examples, a set of speakers arranged onboard the tactile device are used to provide the audio outputs.

The system can include a control module (e.g., within the housing, remote from the housing, onboard a user device, etc.), which functions to apply a stimulation pattern through the actuation subsystem. Additionally or alternatively, the control module can function to determine one or more stimulation patterns (e.g., at a computing subsystem), store one or more stimulation patterns, monitor system performance, implement a fail-safe (e.g., power shut-off in the event of overheating or stimulation pattern parameter above a predetermined threshold, alarm, etc.), and/or perform any other suitable function. Determining a stimulation pattern can include any or all of: determining a new stimulation pattern (e.g., based on an algorithm, based on a machine learning model, etc.), selecting a stimulation pattern (e.g., from a lookup table, from a library, from a record of previously applied stimulation patterns, etc.), determining a set of parameters associated with a stimulation pattern (e.g., a set of weights for a stimulation pattern algorithm, an amplitude a stimulation, a frequency of stimulation, etc.), and/or any other suitable stimulation pattern and/or parameter(s) associated with a stimulation pattern.

The system 100 can optionally include and/or be configured to interface with a user device and/or a client application executing on the user device. The client application preferably enables a user to select one or more operational parameters of the system, such as any or all of: an operation mode (e.g., music mode, conversation mode, quiet mode, on mode, off mode, etc.), an operational parameter (e.g., sensitivity of detected audio, overall amplitude of vibration, etc.), a set of audio outputs to be provided (e.g., in an audio therapy program for tinnitus), and/or any other suitable parameter. Examples of the user device include a tablet, smartphone, mobile phone, laptop, watch, wearable device (e.g., glasses), or any other suitable user device. The user device can include power storage (e.g., a battery), processing systems (e.g., CPU, GPU, memory, etc.), user outputs (e.g., display, speaker, vibration mechanism, etc.), user inputs (e.g., a keyboard, touchscreen, microphone, etc.), a location system (e.g., a GPS system), sensors (e.g., optical sensors, such as light sensors and cameras, orientation sensors, such as accelerometers, gyroscopes, and altimeters, audio sensors, such as microphones, etc.), data communication system (e.g., a WiFi module, BLE, cellular module, etc.), or any other suitable component.

Additionally or alternatively, the system can include any or all of: a power source, a communication module (e.g., a wireless communication module, Wifi chip, Bluetooth module, Bluetooth chip, etc.), and/or any other suitable components.

In a first variation of the system, the system is in the form of a wearable wristband device including a plurality of haptic actuators (e.g., LRA actuators) configured to apply haptic stimulation to a wrist of the user, wherein the wristband device can be in communication with one or more user devices. The tactile device and/or the user device preferably further includes a set of audio speakers configured to provide audio information to a user and/or a sensor system including a set of audio sensors (e.g., microphones) configured to detect audio information in an environment of the user, but can additionally or alternatively include any other suitable components.

Figure 3A:
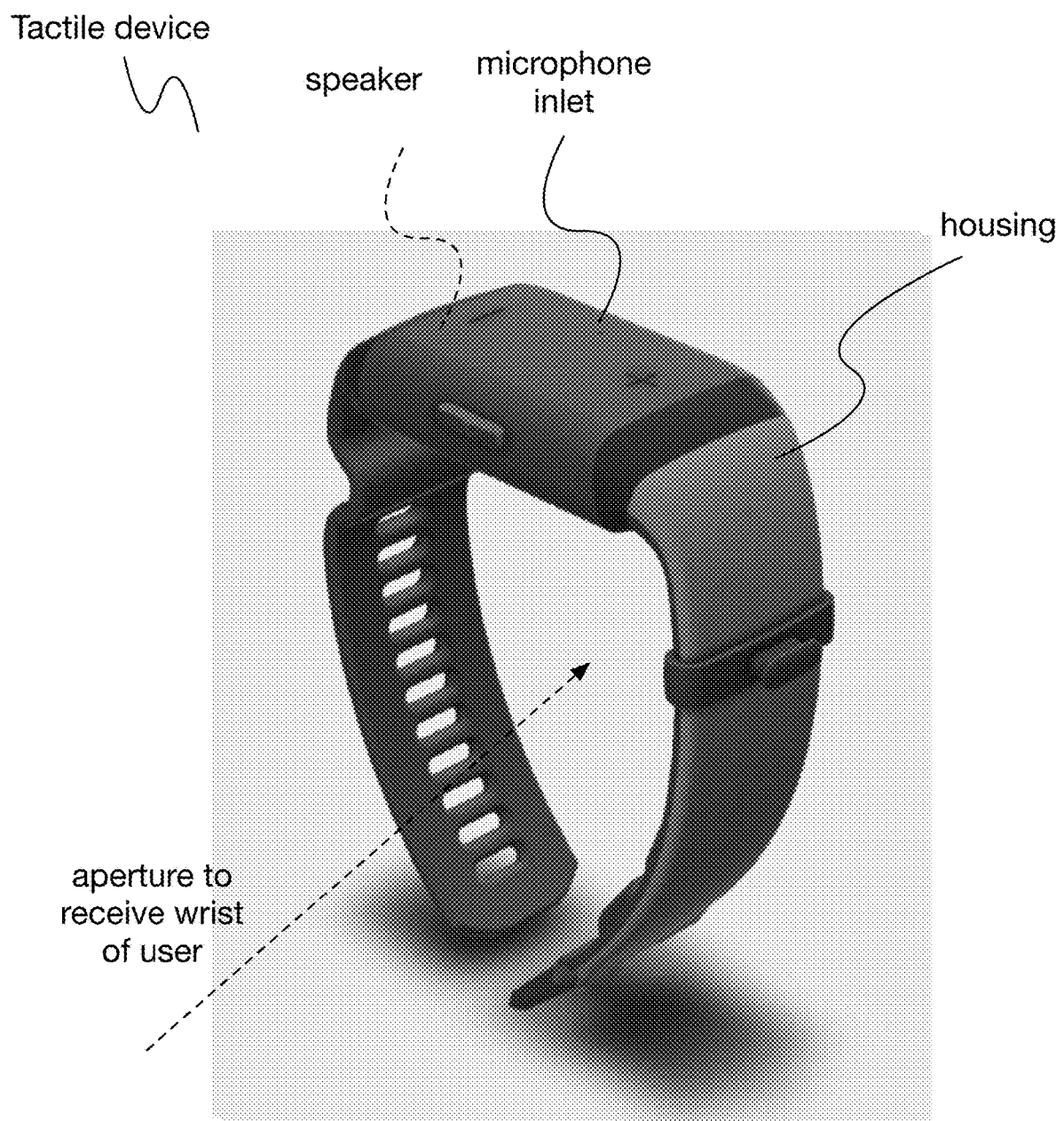
FIGS. 3A-3C depict an example of a tactile device for multimodal stimulation.
Figure 3B:
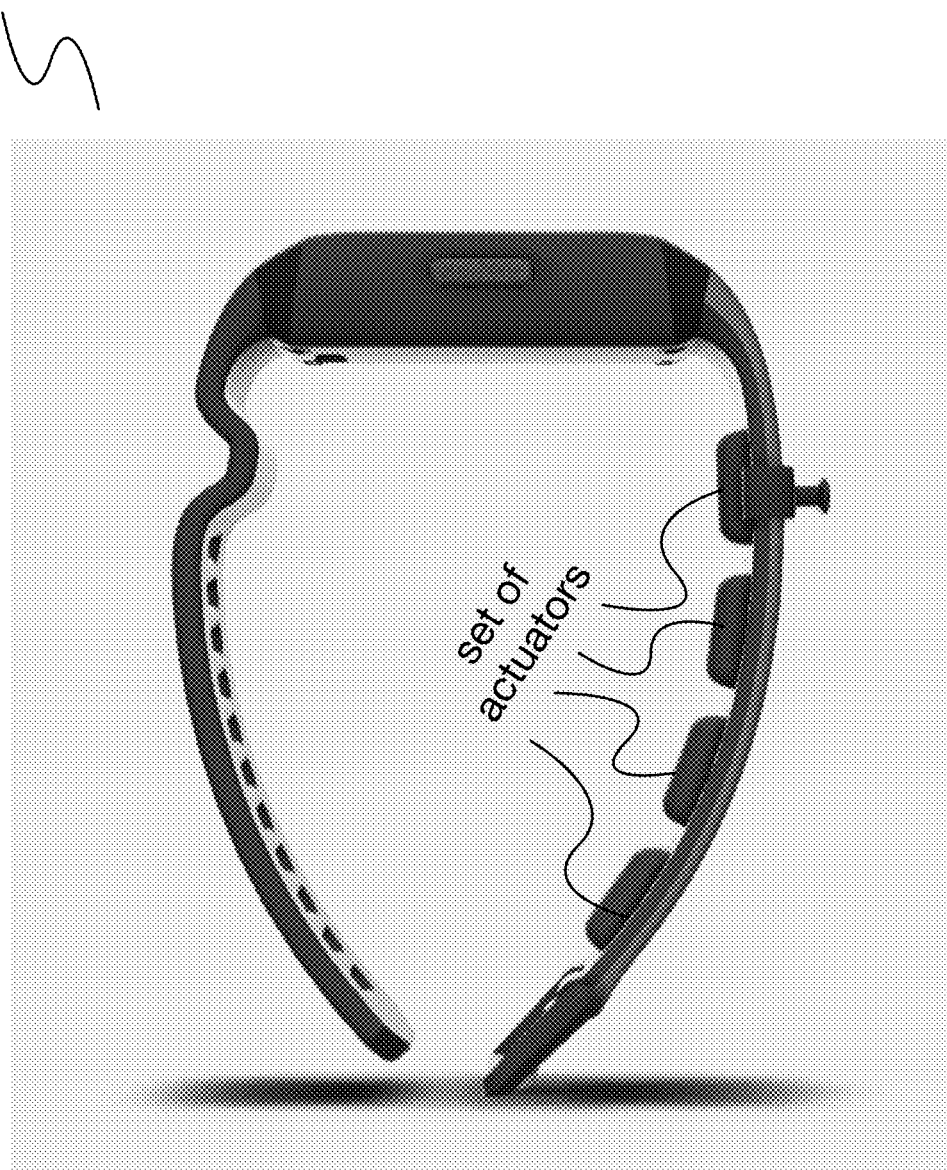
Figure 3C:
Figure 3C:

In specific examples (e.g., as shown in FIGS. 3A-3C), the tactile device includes a wristband haptic stimulation device including an actuator subsystem having a set of one or more actuators arranged at one or more locations of a wrist region of the user (e.g., with a strap, wristband, bracelet, watchband, fabric, etc.), such as around a circumference of the wrist, around a partial circumference of the wrist, at a set of one or more discrete points proximal to the wrist, at any region of the arm and/or hand, and/or at any other suitable regions proximal to the user's wrist(s). Additionally or alternatively, the haptic device can be worn on any other body regions of the user (e.g., torso in a vest embodiments, leg, etc.). The set of one or more actuators can include any or all of: an actuator (e.g., linear resonant actuator [LRA], electroactive polymer [EAP] actuator, electromechanical polymer [EMP] actuator, etc.), a motor (e.g., brushless motor, brushed motor, direct current (DC) motor, alternating current (AC) motor, eccentric rotating mass (ERM), etc.), a piezoelectric device, and/or any other suitable vibratory elements.

Figure 4:
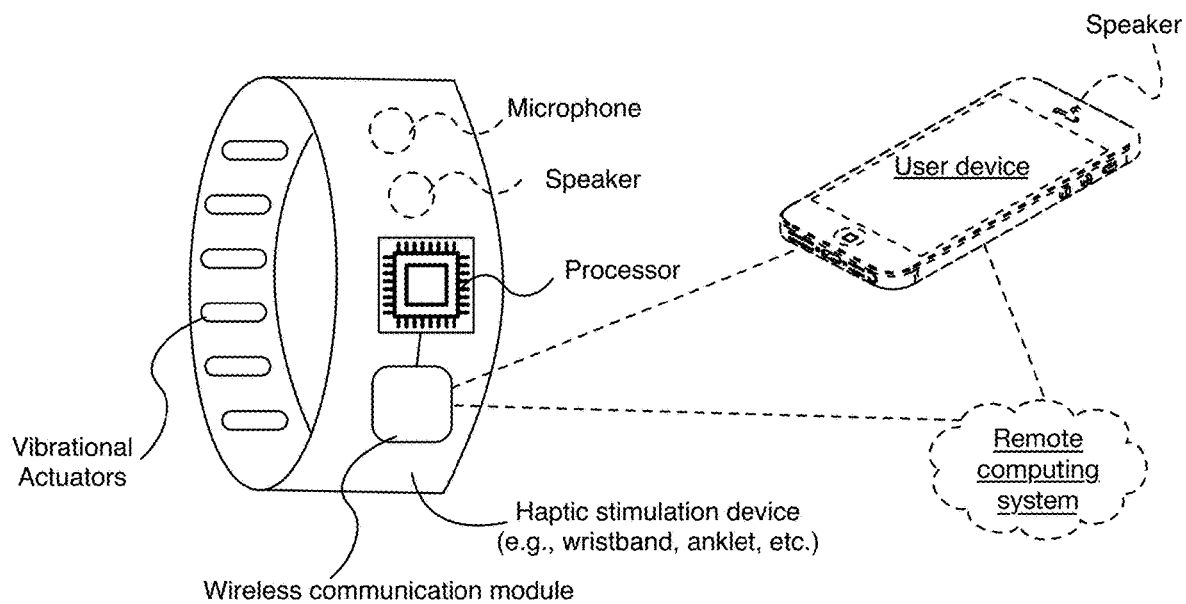
FIG. 4 depicts a variation of a system for multimodal stimulation.

In some variations (e.g., as shown in FIG. 4, as shown in FIGS. 3A-3C), for instance, the haptic stimulation device includes a wristband device including one or more (e.g., 4, 8, between 1 and 10, 1, greater than 10, etc.) actuators (e.g., LRA actuators) arranged around a partial or full circumference of one or both wrists of the user. The wristband device is preferably in communication with a user device and/or computing system (e.g., remote computing system) for processing, receiving inputs (e.g., from sensors, from a user, etc.), providing outputs (e.g., at a client application of the user device), and/or any other functions, but can additionally or alternatively be in communication with any other components.

In other variations (e.g., as shown in FIG. 4), the haptic stimulation device includes an anklet device including one or more (e.g., 4, 8, between 1 and 10, 1, greater than 10, etc.) actuators (e.g., LRA actuators) arranged around a partial or full circumference of one or both ankles of the user. The anklet device is preferably in communication with a user device and/or computing system (e.g., remote computing system) for processing, receiving inputs (e.g., from sensors, from a user, etc.), providing outputs (e.g., at a client application of the user device), and/or any other functions, but can additionally or alternatively be in communication with any other components.

Figure 5:
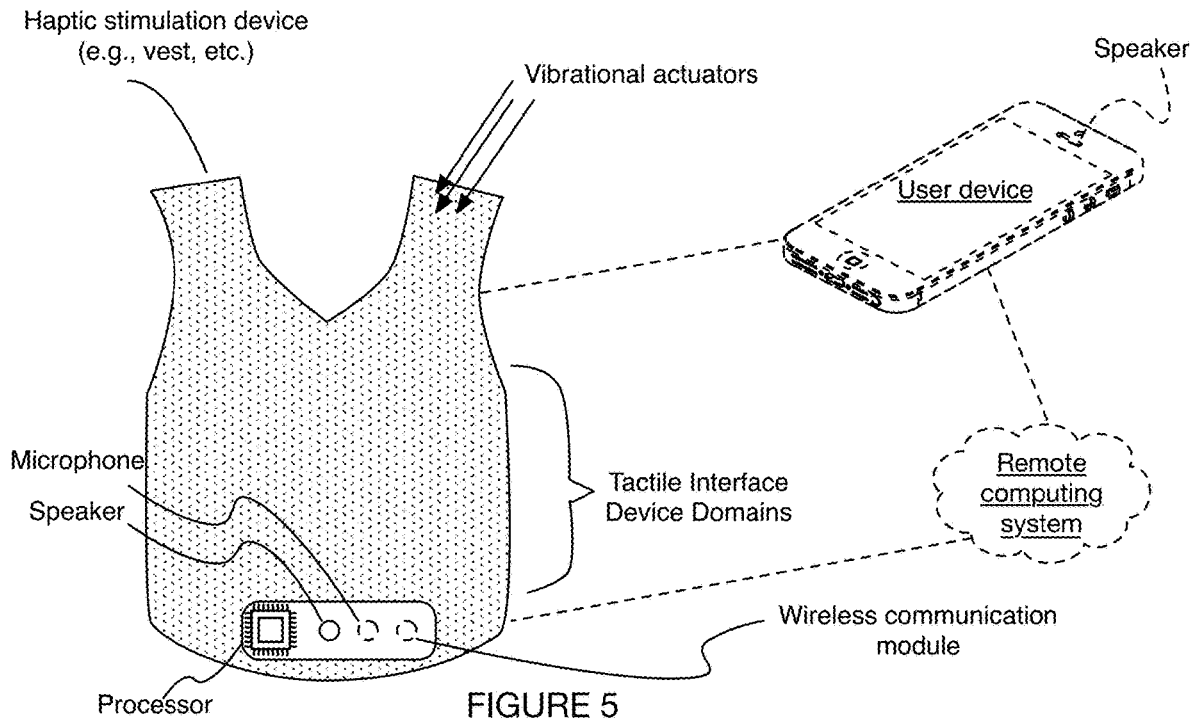
FIG. 5 depicts a variation of a system for multimodal stimulation.

In yet other variations (e.g., as shown in FIG. 5), the haptic stimulation device includes a tactile garment (e.g., haptic vest) including an array of actuators which provide tactile stimulation to a chest and/or back and/or sides of the user. The garment is preferably in communication with a user device and/or computing system (e.g., remote computing system) for processing, receiving inputs (e.g., from sensors, from a user, etc.), providing outputs (e.g., at a client application of the user device), and/or any other functions, but can additionally or alternatively be in communication with any other components.

In other variations of the system, the system can be in the form of another wearable device (e.g., headband, garment, etc.), a non-wearable device, and/or can have any other form factors.

Additionally or alternatively, the system can include any other components.

4. Method 200

As shown in FIG. 2, a method 200 for multimodal stimulation includes determining a set of outputs S200 and providing the set of outputs S300. Additionally or alternatively, the method 200 can include receiving a set of inputs S100, adjusting any or all of the set of outputs S400, and/or any other suitable processes. Further additionally or alternatively, the method 200 can include and/or interface with any or all of the methods, processes, embodiments, and/or examples described in any or all of: U.S. Application Ser. No. 17/033,433, filed 25 Sep. 2020, and U.S. application Ser. No. 17/144,076, filed 7 Jan. 2021, each of which is incorporated in its entirety by this reference, or any other suitable processes performed in any suitable order.

The method 200 functions to provide multimodal stimulation to a user through a multimodal stimulation plan (e.g., a bimodal stimulation plan) which provides multiple types of stimulation (e.g., audio, tactile, visual, etc.) to the user, which can in turn function to alleviate one or more user conditions (e.g., tinnitus), enhance user sensing (e.g., by supplementing audio with tactile stimulation, by enhancing visual information with tactile stimulation, for hearing-impaired individuals, for hearing-abled individuals, etc.), enhance a user experience and/or entertain a user, and/or can perform any other functions.

In a first set of variations, the method 200 functions to mitigate and eliminate the unwanted auditory ringing sensation associated with tinnitus, wherein the multimodal stimulation functions to help enable this mitigation/elimination. Additionally or alternatively, the method 200 can be otherwise implemented.

The method 200 is preferably performed with a system 100 as described above, but can additionally or alternatively be implemented with any other system(s).

4.1 Method—Receiving a Set of Inputs S100

The method 200 can optionally include receiving a set of inputs S100, which functions to receive information with which to determine any or all of the set of outputs. Additionally or alternatively, S100 can function to receive inputs with which to determine one or more operation modes of the system, determine one or more parameters associated with the system, and/or can perform any other function(s).

S100 is preferably performed initially during the method 200 and optionally multiple times during the method 200 (e.g., in response to S300 and/or prior to S400, continuously, at a predetermined frequency, etc.). Additionally or alternatively, S100 can be performed after any other processes of the method 200 and/or the method 200 can be performed in absence of S100.

The set of inputs can be received at any or all of: the tactile device, a user device (e.g., a mobile user device such as a smartphone and/or tablet and/or laptop), any other supplementary device, any combination, and/or at any other devices. The inputs can be received at any or all of: one or more sensors, a client application, one or more input components (e.g., buttons, switches, etc.) of a device, and/or at any other components.

The types of inputs can be any or all of: predetermined (e.g., based on the system, based on the user, etc.), dynamically determined (e.g., based on a current operation mode of the system, etc.), any combination, and/or otherwise determined.

The inputs can be received at any or all of: continuously, at a predetermined frequency, at a predetermined set of intervals, at a random set of intervals, in response to a trigger, and/or at any other times. Alternatively, the method 200 can be performed in absence of receiving a set of inputs S100.

In preferred variations in which the multimodal stimulation includes audio stimulation with tactile stimulation, the set of inputs received in S100 can optionally include audio information from an environment of the user, wherein the audio inputs received (e.g., at a microphone of the tactile device, at a microphone of a user device in communication with the tactile device, etc.) can be used to trigger haptic stimulation, such as contemporaneously with (e.g., in quick succession after, overlapping with, partially overlapping with) the occurrence of the audio information. In specific examples, this can be implemented, for instance in an organic exposure therapy protocol (e.g., as described below) for users experiencing tinnitus.

The audio input is preferably in the form of an audio signal, further preferably an audio waveform, wherein the audio waveform can be processed in accordance with any or all of the subsequent processes of the method. Additionally or alternatively, any other suitable audio input(s) can be received. The audio input is preferably received at a microphone of a sensor subsystem of the system, further preferably a microphone onboard a housing of the tactile interface device. Additionally or alternatively, the audio input can be received from a microphone of a separate sensor subsystem (e.g., onboard a user device), a remote computing system, and/or any other suitable sensor or information source.

The inputs can additionally or alternatively include any or all of: user preferences and/or other user inputs (e.g., indicating a user condition, loudness preferences, tinnitus frequency associated with the user's condition, operation mode selection, etc.), and/or any other inputs.

In some variations, for instance, the user can provide one or more parameters associated with his or her tinnitus condition, such as a frequency and/or loudness associated with his or her tinnitus condition, which is used to determine any or all of the multimodal stimulation plan (e.g., bimodal stimulation plan including audio outputs and tactile outputs) provided to the user (e.g., as described below). In a set of examples, the user enters (e.g., at a client application executing on a user device, at an online survey, at a set of buttons or other user interface onboard the tactile stimulation device, etc.) a set of one or more frequencies which matches the frequency of the tinnitus he or she perceives, which is used to determine the frequency or frequencies of audio outputs (e.g., tones) provided to the user (e.g., as described below). Additionally or alternatively, the user can enter other information associated with his or her tinnitus, such as a perceived loudness at which he or she perceives her tinnitus, one or more temporal features associated with his or her tinnitus (e.g., at what times of day the tinnitus occurs, for how long of a duration each episode of tinnitus lasts, how frequently the tinnitus occurs, etc.), a severity associated with the tinnitus (e.g., based on a scale from 1 to 10), and/or any other information.

In a specific example, the user interacts with a client application to provide a set of features associated with his or her tinnitus, where the client application is configured to play (e.g., with a speaker of the user device) audio of various frequencies (e.g., set of tones with increasing frequency, frequency slider bar, etc.), where a user indicates (e.g., selects, approves, etc.) the frequency which most closely matches his or her tinnitus. The user can additionally select a loudness (e.g., with a volume slider bar, based on the volume of his or her user device, etc.) associated with the tinnitus condition. The loudness can optionally be used to determine: any or all of the audio outputs of the bimodal stimulation plan (e.g., to match the loudness of his or her tinnitus), any or all of the tactile outputs of the bimodal stimulation plan (e.g., to prescribe a higher intensity of vibration for a higher loudness selection), and/or any other features of the bimodal stimulation plan. Additionally or alternatively, the loudness can be used to determine a progress metric associated with the user's tinnitus as he or she receives therapy through the bimodal stimulation plan, which can optionally be used, for instance, to adjust any or all of the bimodal stimulation plan (e.g., as described below). As the user's tinnitus condition improves (e.g., decreases in loudness), for instance, the client application can decrease a number of times per day that it recommends to the user to perform the bimodal stimulation, decrease a duration of the bimodal stimulation, adjust frequencies (e.g., decrease a range of frequencies, increase a range of frequencies, etc.) or loudnesses of the audio output, adjust stimulation parameters (e.g., amplitude, intensity, etc.) associated with the tactile stimulation device, and/or otherwise adjust the therapy provided to the user. Additionally or alternatively, the progress metric can be based on any other features, such as a severity of tinnitus indicated by the user, temporal parameters associated with the user's tinnitus, and/or any other features.

The user can additionally or alternatively provide any other information, such as, but not limited to, any or all of: demographic information (e.g., age, sex, ethnicity, etc.), historical information (e.g., history of tinnitus experience, medical history, family history, etc.), lifestyle information (e.g., fitness level, career information, etc.), and/or any other information.

In a first variation, S100 includes receiving a set of inputs associated with features of the tinnitus condition experienced by the user. The features preferably include a frequency value and/or range of frequency values and optionally a loudness associated with the tinnitus condition, but can additionally or alternatively include other features (e.g., how often the user experiences tinnitus, how long each day the user typically experiences tinnitus, a severity associated with the user's tinnitus, etc.).

In a second variation, additional or alternative to the first, S100 includes receiving audio inputs from an environment of the user at one or more microphones associated with the system (e.g., onboard the tactile stimulation device, onboard the user device, etc.), where the audio inputs are processed (e.g., to determine a frequency associated with the environmental audio, to determine a loudness associated with the environmental audio, etc.) and used to determine and trigger tactile stimulation to be provided to the user (e.g., with a minimal time delay from the occurrence of the environmental audio).

Additionally or alternatively, any other inputs can be received in S100 and/or S100 can include any other suitable processes.

4.2 Method—Determining a Set of Outputs S200

The method includes determining a set of outputs S200, which functions determine the features of the multimodal stimulation plan to be applied to the user. Additionally or alternatively, S200 can function to optimize the multimodal stimulation to be delivered to the user (e.g., based on historical information associated with another user, based on the user's therapy history, etc.) and/or can perform any other functions.

S200 can optionally be performed based on and/or in response to S100, but can alternatively be performed in absence of S100 and/or at any other suitable times or in response to any other information and/or triggers. As such, any or all of the outputs can be determined based on the set of inputs, determined independently of the set of inputs, determined based on any other information, any combination, and/or otherwise determined.

The outputs are preferably collectively provided at the tactile stimulation device and the user device, but can additionally or alternatively be provided at other devices (e.g., multiple user devices, supplementary devices, etc.), a single device (e.g., all at the tactile stimulation device, all at the user device, etc.), and/or any other devices or combination of devices.

S200 can optionally include determining a $1^{st}$ set of outputs S210, wherein the $1^{st}$ set of outputs preferably includes non-tactile outputs, such as any or all of: audio outputs, visual outputs, and/or any other suitable outputs. Alternatively, the $1^{st}$ set of outputs can be include tactile outputs and/or S200 can be performed in absence of determining a $1^{st}$ set of outputs.

The $1^{st}$ set of outputs can be predetermined, dynamically determined (e.g., based on inputs received in S100), or any combination.

The $1^{st}$ set of outputs preferably includes (e.g., in cases of tinnitus therapy), a set of audio outputs (e.g., provided at a set of one or more speakers) provided at one or more speakers of the system. The set of speakers preferably includes a speaker at the user device, but can additionally or alternatively include a speaker onboard the tactile stimulation device, a combination of speakers, and/or any other speakers arranged at any suitable devices.

Alternatively, the user can experience audio outputs organically in his or her environment (e.g., for organic exposure therapy) and/or the user can receive any other outputs in the $1^{st}$ set of outputs.

The set of audio outputs preferably includes a plurality of different sounds (e.g., sounds having different frequencies, different durations, different intensities, etc.), but can additionally or alternatively include a single sound, multiple identical sounds, and/or any other sounds. Each of the sounds is preferably a tone, further preferably a tone associated with a single frequency (e.g., pure tone, sine tone, etc.). Additionally or alternatively, any or all of the sounds can include sounds having multiple frequencies (e.g., complex tone, fundamental tone with overtone(s) and/or harmonic(s), etc.), and/or can include any other sounds (e.g., notes, music, etc.).

In variations involving tone-based therapy (e.g., for tinnitus), for instance, the audio outputs include a set of tones, further preferably a set of pure sine tones, but can alternatively include any other types of tones or sounds. In another set of examples involving tone-based therapy, the audio outputs include a set of tones having frequency values both lower and higher than (e.g., logarithmically centered around) a frequency value associated with the user's tinnitus. In yet another set of specific examples, the audio outputs include music.

In additional or alternative variations, the audio outputs can include sounds having multiple tones and/or frequencies, and/or any other suitable audio. In some variations, for instance any or all can be played: a set of one or more sounds having multiple frequencies (e.g., multiple tones overlaid and/or played simultaneously, combination tones, complex tones, etc.), which can function to increase the frequency spread of the audio experienced by the user (e.g., to ensure that the frequency or frequencies associated with the user's tinnitus are played); music, which can function to be more pleasing to the user and/or can increase the number of frequencies played; and/or any other sounds.

Additionally or alternatively, the sounds can have any suitable quality and/or prescribed waveforms, such as, but not limited to: sine tones, square waves, sine wave with a single harmonic, sine wave with multiple harmonics, ramps, and/or any other sounds.

Further additionally or alternatively, the sounds can optionally have any suitable timbre, such as a timbre on top of a sine wave (e.g., to indicate a different musical instrument), and/or any other suitable sounds.

The set of audio outputs can be provided with any volume or set of volumes (e.g., phon scale loudness), such as any or all of: a constant loudness among all sounds; a loudness which varies based on frequency or other parameters; random loudness values for each sound; loudness value(s) determined based on a user input (e.g., loudness of user's tinnitus); loudness value(s) determined based on user preferences; a set of loudness values set according to an equal-loudness counter curve; and/or any other loudness/volume parameters.

Frequency values associated with the audio outputs provided to the user are preferably determined, at least in part, based on a frequency associated with the user's tinnitus, such as a frequency value received from the user as an input in S100. In preferred variations, for instance, the frequency value associated with the user's tinnitus is used to select a range of frequencies for the sounds in the set of audio outputs (e.g., tone frequencies). In some examples, frequency values for the sounds are selected to be centered around (e.g., on a logarithmic scale, on a linear scale, on a semitone scale, etc.) and/or substantially centered around a frequency value associated with the user's tinnitus (and optionally including the frequency value associated with the user's tinnitus). In a particular specific example involving tonal sounds, which equivalently refers to herein as any tones (e.g., pure tones, sine tones, etc.), a first octave of tones below the frequency associated with the user's tinnitus and a second octave of tones above the frequency associated with the user's tinnitus are selected to form the set of audio outputs. Additionally or alternatively, any other sounds (e.g., non-pure tones) can be provided and optionally centered around the user's tinnitus frequency or frequencies.

The frequencies of the sounds are preferably between 500 and 8000 Hertz (Hz) (e.g., between 500-1000 Hz, between 500-2000 Hz, between 1000-2000 Hz, between 3000-8000 Hz, etc.), but can additionally or alternatively be 500 Hz or less (e.g., between 400-500 Hz, between 300-400 Hz, between 200-300 Hz, between 100-200 Hz, less than 100 Hz, etc.), 8000 Hz or more (e.g., between 8000-10000 Hz, etc.), and/or any combination. Additionally or alternatively, any or all of the frequencies can be determined based on a frequency associated with a condition of the user (e.g., as described above), such as a frequency at which the user hears the ringing associated with his or her tinnitus (e.g., pure tone tinnitus, varied tone tinnitus, etc.), a frequency associated with a user's hearing loss (e.g., a frequency or range of frequencies which the user cannot hear, for suspected early-stage tinnitus, etc.), and/or any other parameters.

Additionally or alternatively, the sounds can be determined in absence of a user's tinnitus frequency (e.g., based on a predetermined set and/or schedule of sounds), the sounds can be determined based on a predicted tinnitus frequency (e.g., as determined with a machine learning model), the same sounds can be provided to all users (e.g., regardless of his or tinnitus frequency), the sounds can be randomly selected, and/or the sounds can be otherwise suitably determined.

The frequency values associated with the sounds can additionally or alternatively be determined and/or selected according to a scale, such as any or all of: a linear scale, a nonlinear scale (e.g., logarithmic scale, pentatonic scale, etc.), a semitone-spaced scale, any combination, and/or any other scale(s). In preferred variations including tonal sounds (e.g., pure tones), for instance, a set of tonal sounds are selected which are evenly spaced along a logarithmic scale. Additionally or alternatively, frequency values can be selected to be evenly spaced on a linear scale, selected to be unevenly spaced on a scale (e.g., linear scale, nonlinear scale, etc.), spaced at semitone intervals, selected based on a combination of scales, and/or otherwise selected.

The sounds of the set of audio outputs are preferably played to the user in a series, wherein an order of the series is further preferably randomized with a randomization process (e.g., random number generator, pseudo-random number generator, etc.). This can function to randomly alternate the sounds of the set which are played to the user such that the user cannot anticipate which sound is coming next—in some cases, this lack of ability for the user to anticipate which sound is coming next has been shown by the inventors to increase the effectiveness of the therapy. In a set of preferred variations, for instance, the order in which a set of audio outputs (e.g., tones, pure tones, etc.) is played is randomized with respect to the frequency/frequencies of the audio outputs such that the user cannot anticipate which frequency/frequencies the next audio output played will have.

Additionally or alternatively, the sounds can be played in a predetermined order (e.g., in order of increasing frequency, in order of decreasing frequency, etc.), according to a pattern, and/or in any other way(s).

In an alternative set of variations, for instance, the set of sounds includes a set of tones (e.g., pure tones) having a plurality of frequencies applied in an ordered sequence (e.g., of increasing frequency, of decreasing frequency, of alternating frequency, of increasing and then decreasing frequency, etc.).

The set of audio outputs is preferably associated with a set of temporal parameters, such as any or all of: a timing at which the sounds are played; a duration for which each sound is played; a temporal delay between adjacent tones; a number of times the set of audio outputs is repeated in the bimodal stimulation plan; a total duration of the bimodal stimulation plan; and/or any other temporal parameters.

The set of audio outputs is preferably configured to be provided contemporaneously with a set of tactile outputs, such as at any or all of: at the same time, at overlapping times, at partially overlapping times, in close proximity in time (e.g., within less than 1 second of each other, within less than 100 milliseconds (ms) of each other within less than 10 ms of each other, within less than 1 ms of each other, within between 1 and 10 ms of each other, within between 10 and 100 ms of each other, between 100 and 500 ms of each other, between 1 and 500 ms of each other, etc.), or otherwise occurring in time. Alternatively, the audio outputs can be provided at different times than the haptic outputs, at one or more times relative to other types of outputs, and/or at any other time(s).

The set of audio outputs is preferably configured to be played with a delay between adjacent sounds, wherein the delay is further preferably a variable delay. The variable delay is preferably determined with a randomization process (e.g., same randomization process as described above for determining a random sequence for the sounds, different randomization process, etc.), such that the user cannot anticipate when exactly the next sound will play (e.g., to make the bimodal stimulation plan more effective in alleviating the user's tinnitus). In some variations, for instance, the delay between adjacent sounds (e.g., between $1^{st}$ and $2^{nd}$ sounds, between $2^{nd}$ and $3^{rd}$ sounds, etc.) is randomly determined based on an average delay (e.g., 500 ms, 400 ms, 600 ms, between 200 ms and 800 ms, between 300 and 700 ms, between 400 and 600 ms, between 100 and 1000 ms, etc.). Additionally or alternatively, there can be a constant delay between adjacent sounds, a delay determined according to a pattern (e.g., increasing delay, decreasing delay, decreasing delay then increasing delay, etc.), no delay (e.g., immediate playing of next sound, overlapping, etc.), a dynamically determined delay, and/or any combination.

The audio output can be played for any suitable duration or durations. The duration(s) are each preferably less than 10 seconds, further preferably less than 1 second (e.g., between 500 and 1000 ms, between 200 and Boo ms, between 300 and boo ms, between 10 and 1000 ms, etc.), but can additionally or alternative have durations of greater than 1 second (e.g., between 1 second and 2 seconds, between 2 and 8 seconds, between 5 and 10 seconds, etc.). For variations including a series of tones, for instance, each of the set of tones can be played for the same duration, different durations, or any combination. In some variations, the duration of each sound is determined with a randomization process (e.g., based on an average duration value). Additionally or alternatively, the durations can be constant among sounds, determined according to a pattern, predetermined, dynamically determined, and/or otherwise determined.

The set of audio outputs can optionally be looped and/or otherwise repeated in the multimodal stimulation plan provided to the user, such that any or all of the set of audio outputs are played multiple times during a therapy session, where a therapy session refers to a provision of the multimodal stimulation plan. In a preferred set of variations, for instance, the set of audio outputs are played multiple times (e.g., for a total duration such as a total duration of 10 minutes, for a predetermined number of repeats, etc.) during the multimodal stimulation plan. In a set of specific examples, each of the sounds in the set of audio outputs is played once before repeating another sound (equivalently referred to herein as played without replacement), where the repeated sounds are also played in a random order (e.g., new random order relative to the previous instance of playing the sounds) and/or with random delays and/or durations (e.g., new random delays and/or durations). Alternatively, the playing of the sounds can be further randomized and/or otherwise played with replacement, played in the same way as the previous set of sounds (e.g., same set of delays and/or order and/or durations), and/or any combination.

In a first preferred variation of S210, S210 includes determining a $1^{st}$ set of outputs, wherein the $1^{st}$ set of outputs includes a set of audio outputs to be provided to a user through set of speakers (e.g., at the tactile device, at a user device, etc.).

In a first set of specific examples, the audio outputs include a set of tones (e.g., pure tones) determined based on a frequency value associated with the user's tinnitus condition, wherein the audio outputs include a predetermined number of tones (e.g., 6 tones, 12 tones, between 5 and 15 tones, 10 tones, 20 tones, between 10 and 20 tones, greater than 20 tones, an octave of tones, multiple octaves of tones, octave of 6 tones, etc.) below and/or up to the frequency value of the user's tinnitus, a predetermined number of tones (e.g., 6 tones, 12 tones, between 5 and 15 tones, 10 tones, 20 tones, between 10 and 20 tones, greater than 20 tones, a next octave of tones, multiple octaves of tones, octave of 6 tones, etc.) above and/or at the frequency value of the user's tinnitus, and optionally the frequency value of the user's tinnitus. The tones are preferably spaced along a logarithmic scale, but can additionally or alternatively be linearly spaced, spaced along a predetermined scale (e.g., semitone scale), randomly spaced, and/or any combination. The order in which the tones are played is preferably randomized along with the delays between adjacent tones, but can additionally or alternatively be predetermined and/or otherwise ordered. The tones are preferably repeated without replacement, wherein the repeated tones have their own randomized order and/or randomized delays, but can additionally or alternatively be otherwise played. Additionally or alternatively, any other audio outputs (e.g., non-pure tones) can be played.

Additionally or alternatively, the audio outputs can include any number of audio outputs.

In a second set of specific examples, the audio outputs include a set of pure tones having multiple frequencies along with a time delay (e.g., constant, variable, etc.) between each tone, wherein the tones increase in frequency based on a scale (e.g., logarithmic, linear, etc.) and then decrease in frequency based on the scale, which can then optionally be repeated for the duration of the multimodal stimulation plan.

Additionally or alternatively, the audio outputs can include any number of partial tones.

In a third set of specific examples, the audio input includes a set of sounds each having multiple frequencies (e.g., multiple overlaid frequencies).

In a fourth set of specific examples, the audio output include a music stream having various frequencies, which can be associated with and/or unrelated to a frequency value associated with the user's tinnitus.

In additional or alternative variations, audio can occur naturally in the environment of the user, wherein this detected audio is used to determine the 2nd set of outputs.

In specific examples, no audio output is provided by the system. In alternative specific examples, additional audio output (e.g., corresponding to the environmental audio, as determined above, independent of the environmental audio, etc.) is provided by the system.

S200 preferably includes determining a $2^{nd}$ set of outputs S220, wherein the $2^{nd}$ set of outputs further preferably includes tactile outputs (equivalently referred to herein as haptic outputs) (e.g., vibratory stimulation) provided at the tactile stimulation device (e.g., at a set of vibratory motors of the device), but can additionally or alternatively include any other outputs. The 2nd set of outputs is preferably determined based at least in part on the $1^{st}$ set of outputs (e.g., temporal parameters of the $1^{st}$ set, frequency parameters of the $1^{st}$ set, etc.), but can additionally or alternatively be determined based on the set of inputs received in S100 and/or any other suitable information.

In variations including an actuation subsystem having a set of one or more tactile actuators, determining the 2nd set of outputs can include determining any or all of: which actuators to actuate (e.g., to produce a tactile sensation at the location of the actuator, to produce a tactile sensation at a location between actuators, etc.), which parameters to actuate the actuators with (e.g., frequency, amplitude, temporal parameters, etc.), and/or any other information.

The tactile outputs are preferably determined based on the $1^{st}$ set of outputs, further preferably a $1^{st}$ set of audio outputs, wherein the tactile outputs are provided in relation to (e.g., in response to, contemporaneously with, etc.) the audio outputs, such that as the audio outputs change, the tactile outputs change. Additionally or alternatively, the tactile outputs can be determined based on environmental audio and/or otherwise determined.

The location of each of the tactile outputs is further preferably determined based on the frequency values associated with the set of set of audio outputs (and/or environmental audio experienced by the user), such that the location of the tactile outputs represents a frequency associated with a corresponding sound in the set of audio outputs (and/or environmental audio experienced by the user) (e.g., location for a higher frequency is to the right of a location corresponding to a lower frequency, based on a linear scale, based on a logarithmic scale, etc.). The location preferably refers to a location on a skin surface of the user at which the user perceives a tactile sensation (e.g., vibration) based on actuation of any or all of the set of actuators onboard the tactile stimulation device. The location can correspond to any or all of: the location of an actuator (e.g., skin region in contact with an actuator such as directly underneath an actuator), a location between actuators which is stimulated based on illusion-based stimulation (e.g., with a funneling tactile effect based on the simultaneous actuation of two or more actuators), and/or any other locations.

The tactile output locations can optionally be determined based on a set of predetermined mappings, wherein each tactile actuator is associated with one or more frequencies, and wherein audio outputs (or audio inputs from S100) are mapped to tactile actuators and/or features of the tactile actuators (e.g., amplitudes) based on their frequencies. Additionally or alternatively, the mappings can be determined based on and/or associated with other parameters (e.g., loudness), other outputs, other information, and/or otherwise determined. Further additionally or alternatively, any or all of the mappings can be dynamically determined.

Figure 9A:
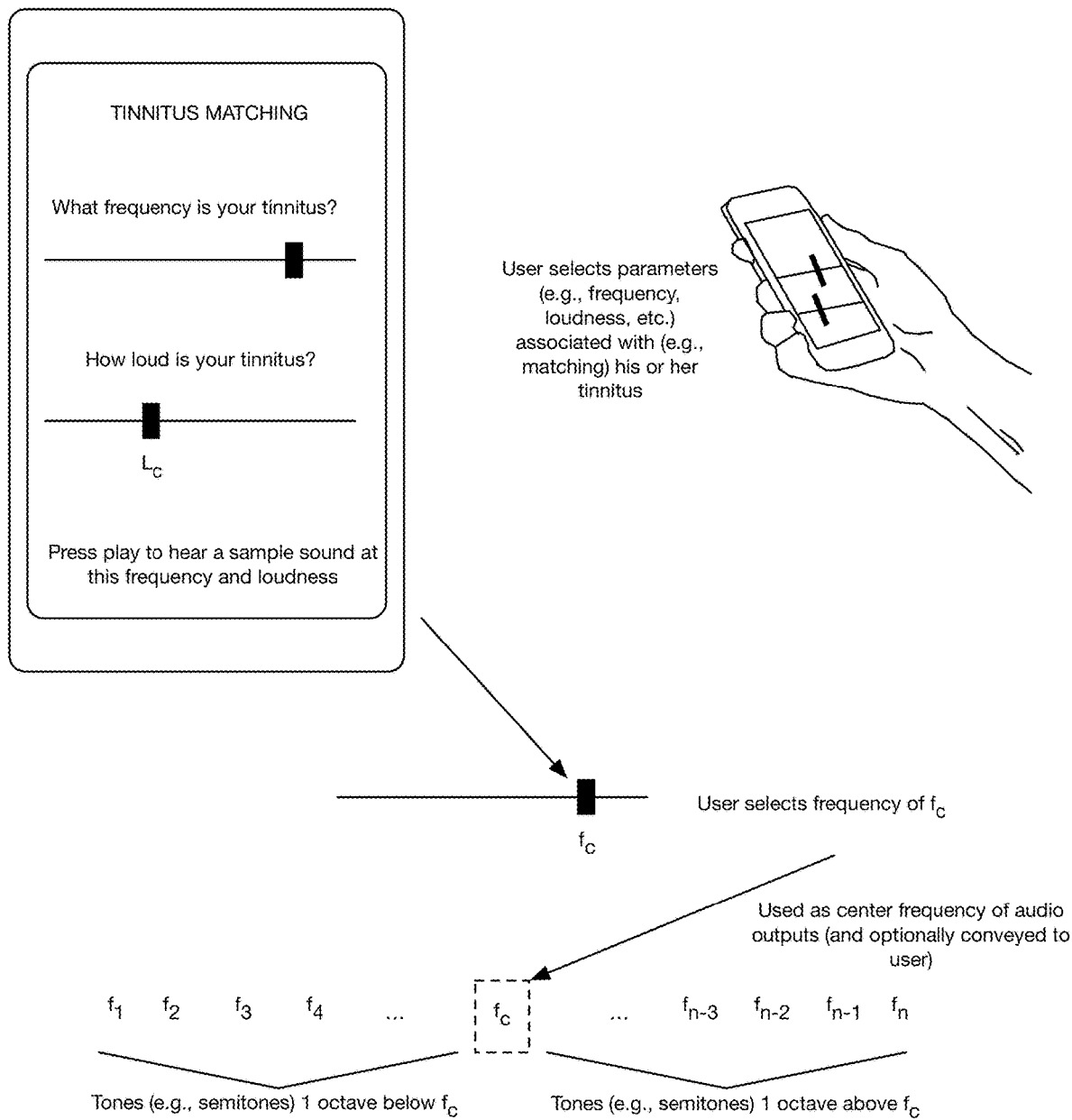
Figure 9C:
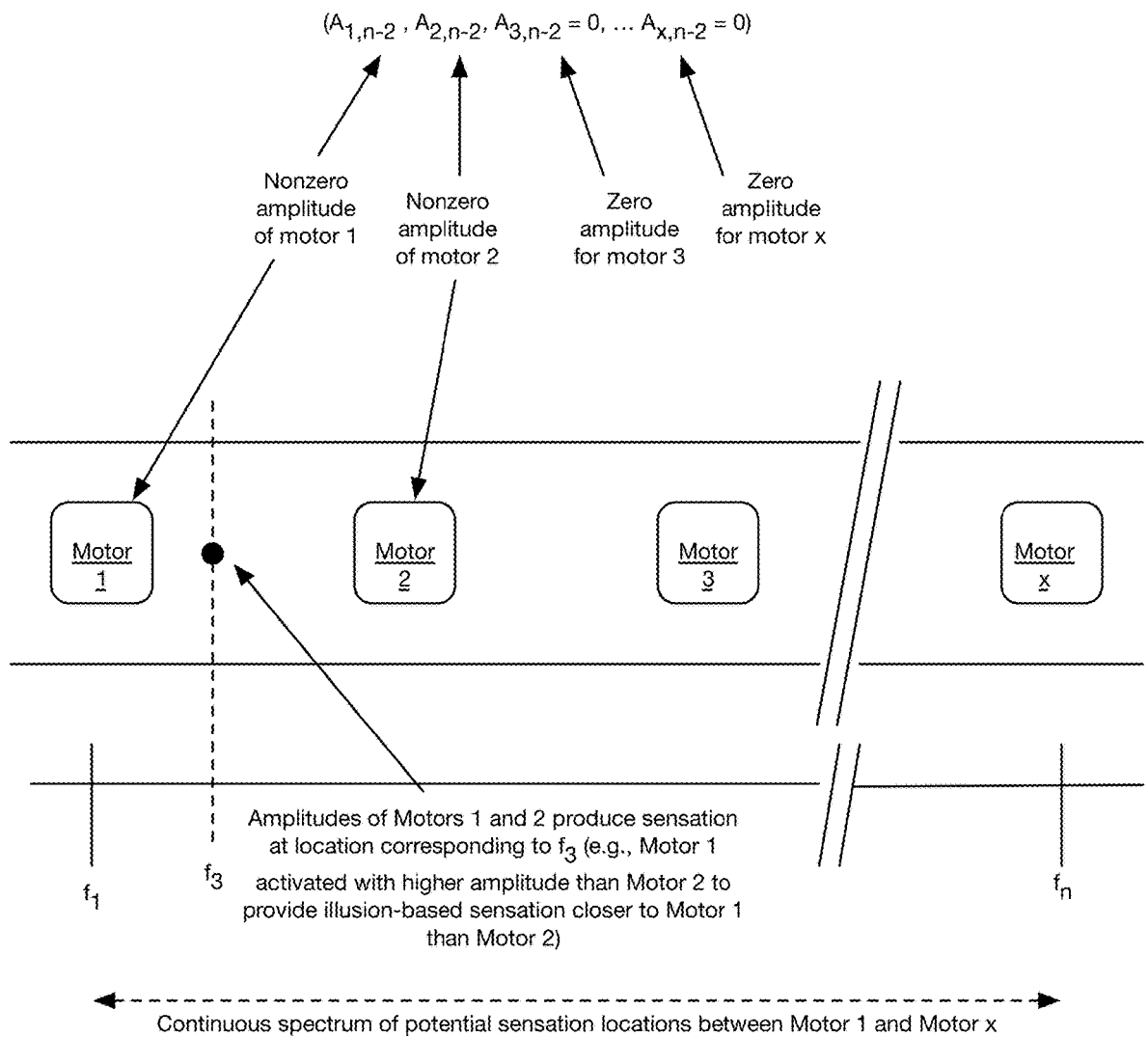
Figure 9D:
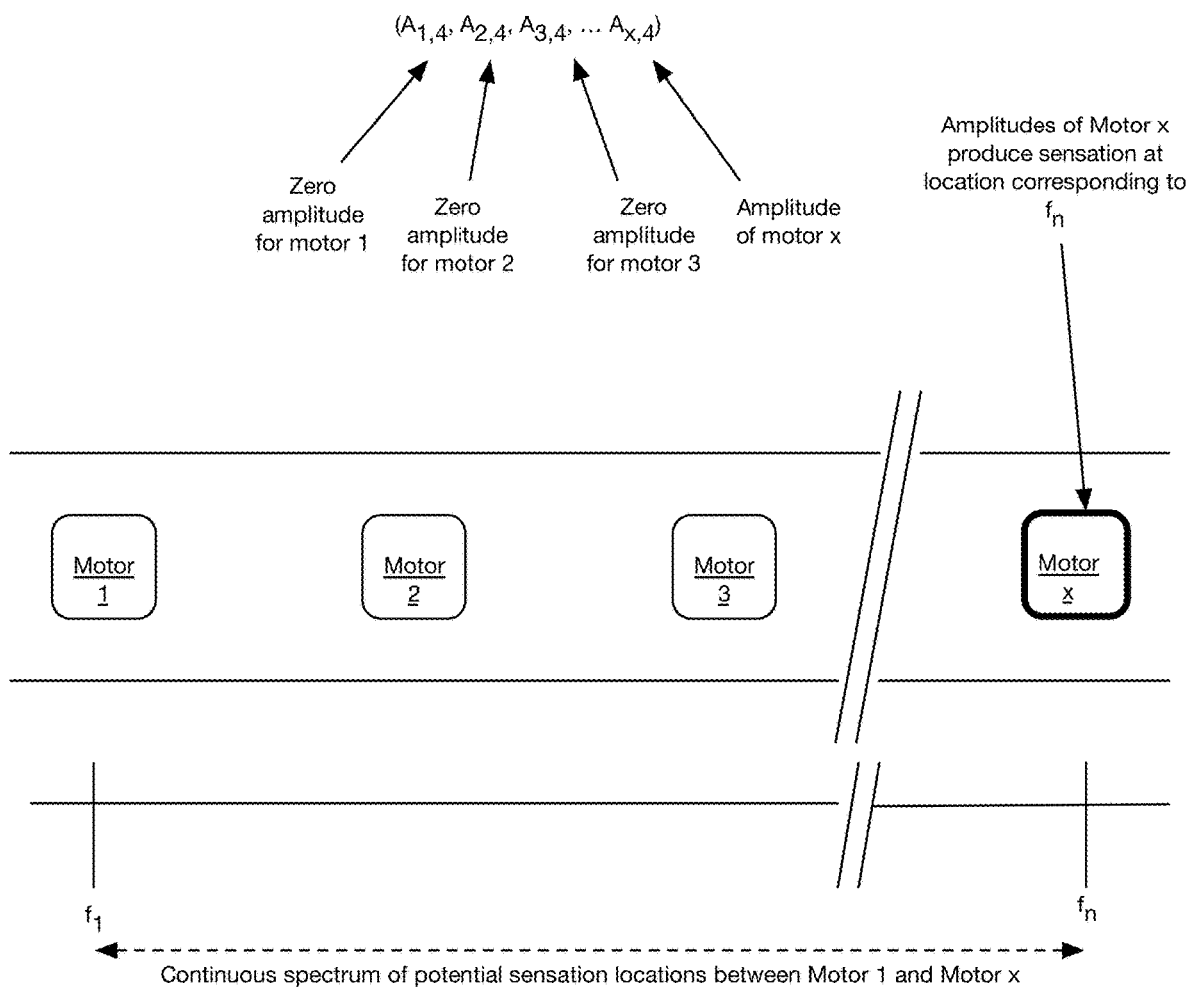

In variations which produce tactile outputs at locations between actuators through illusion-based tactile effects, the illusion-based tactile effect preferably includes a funneling tactile effect at which a tactile sensation between actuators is produced by actuating two or more actuators simultaneously. If two actuators are actuated with the same amplitude, for instance, a tactile sensation can be felt at a location in the center between the two actuators. By actuating the actuators with different amplitudes simultaneously, a virtual location can be produced closer to the actuator with the higher amplitude (e.g., as shown in FIG. 9C). Additionally or alternatively, the actuators can be actuated with other tactile effects (e.g., saltation), in absence of tactile effects, and/or any combination.

In a preferred set of variations, for instance, a continuous spectrum of locations is defined for the user and able to be stimulated based on tactile stimulation with illusion-based stimulation. In a set of specific examples (e.g., as shown in FIG. 9C), the continuous spectrum of locations is defined between and include the locations of a first motor arranged closest to a first end of the tactile device and a last motor arranged closes to an opposing end of the tactile device, wherein the location which is stimulated for each tactile output is determined based on the frequency value(s) of a corresponding audio output and/or environmental audio.

Any or all of the features and/or parameters associated with the tactile output (e.g., stimulation patterns), can additionally or alternatively be determined based on the $1^{st}$ set of outputs and/or the set of inputs. An amplitude and/or intensity of vibration of the tactile actuators, for instance, can optionally be determined (e.g., proportionally, based on a predetermined mapping, based on a nonlinear mapping, based on a linear mapping, etc.) based on a loudness of the audio output and/or environmental audio detected.

The temporal parameters associated with the $2^{nd}$ set of outputs are preferably determined based on temporal parameters associated with the $1^{st}$ set of outputs and/or the set of inputs (e.g., environmental audio), such that the outputs are provided in S300 at any or all of: contemporaneously (e.g., overlapping, partially overlapping, simultaneously, with an undetectable offset, etc.), in close proximity (e.g., within less 1 second of each other, within 10 milliseconds of each other, within 1 millisecond of each other, etc.), with a predetermined delay between an output of the $1^{st}$ set and an output of the $2^{nd}$ set, with a predetermined delay between an input (e.g., environmental audio) and an output of the $2^{nd}$ set, and/or at any other time(s).

In a preferred set of variations, for instance, the tactile outputs are actuated contemporaneously (e.g., simultaneously, in real time, in near real time, with less than 1 ms delay, with less than a 5 ms delay, etc.) with the set of audio outputs played for the user such that the user receives the tactile stimulation at the same time that he or she hears a corresponding sound, which can function to train the user to associate sounds that he or she hears in his or her environment (e.g., through the audio outputs) with tactile stimulation. This can improve the user's tinnitus condition, since the ringing that he or she "hears" internally is not associated with tactile stimulation, which the user then learns to ignore and/or not process.

In an alternative set of variations, the tactile outputs are actuated with a minimal delay (e.g., less than 5 ms, less than 10 ms, less than 100 ms, less than 500 ms, between 5 and 100 ms, between 5 and 500 ms, etc.) relative to audio which naturally occurs in an environment of the user, such that the user receives the tactile stimulation just after (or effectively in real time with the) time that he or she hears the source sound, which can function to train the user to associate sounds that he or she hears in his or her environment (e.g., through the audio outputs) with tactile stimulation. This can improve the user's tinnitus condition, since the ringing that he or she "hears" internally is not associated with tactile stimulation, which the user then learns to ignore and/or not process.

Additionally or alternatively, any or all of the features and/or parameters of the tactile output can be predetermined (e.g., based on a product specification of the tactile actuator, based on a fixed frequency of an LRA, based on a user preference, etc.), determined based on other information, and/or otherwise determined.

Additionally or alternatively, any or all of the tactile output features and/or parameters can be determined with one or more algorithms, such as any or all of the algorithms described in U.S. Application Ser. No. 17/144,076, filed 7 Jan. 2021, which is incorporated herein in its entirety by this reference.

In some variations, for instance, in which environmental audio is detected and used to determine the tactile outputs, an algorithm can be used which is frequency-based, using a discrete Fourier transform to analyze the amplitudes of different frequencies present in the sound and organize into a set of groupings (e.g., set of bins from 300 to 7500 Hz). After calculating a set of amplitudes and/or energies associated with the frequencies present, the algorithm chooses which frequency (e.g., loudest frequency, frequency within a predetermined range relative to the frequency of the user's tinnitus, frequency closest to the user's tinnitus frequency, etc.), if any, should be represented on the wristband. In specific examples, the algorithm chooses the frequency with the greatest amplitude, so long as it is above its own running mean. That is, if a frequency bin contains the greatest amplitude in a given frame but has an amplitude less than that of its running mean (e.g., calculated based on the amplitudes of that bin over the previous frames), the next loudest frequency bin will be chosen by the algorithm instead. This results in the wristband not representing constant, loud hums, such as an AC unit. A frequency bin can also have a minimum amplitude requirement (e.g., an amplitude of at least 20 dB SPL). The amplitude of the vibration can optionally be related to the amplitude of the chosen frequency bin. A minimum amplitude vibration corresponds to a frequency bin amplitude just above that frequency bin's running mean. A maximum vibration amplitude corresponds to the algorithm's current dynamic ceiling, which is a changing value based on the amplitude of recent sounds in any frequency bin. When a loud sound happens, the dynamic ceiling can jump up to the level of that loud sound and then gradually fall over time (if the sound is no longer as loud). By means of this dynamic ceiling, quiet sounds in a quiet environment can be felt with significant amplitude but the same quiet sounds in a loud environment will register as weak. This is comparable to dynamic range compression. Any vibration amplitude between the minimum and maximum values can optionally be scaled based on an exponential curve. This can function to account for Weber's Law, for instance, which dictates that two high-amplitude stimuli require a greater difference in amplitude than two low-amplitude stimuli for a participant to recognize a difference. The algorithm then translates this frequency and amplitude into a motor output by mapping frequency onto one or more different spatial locations, which can optionally leverage the phenomenon of a haptic illusion. Specifically, an illusory location is a point on the wrist that is felt by the wearer of the wristband even when a motor is not located directly at that point. These illusion locations can be stimulated for instance by turning on two motors, one on either side of the illusion location, at specific amplitudes such that the wearer feels as if a single point somewhere between the two motors is vibrating. The algorithm is designed in this way with the aim of representing environmental sounds such that very different sounds feel very different and very similar sounds feel very similar.

Additionally or alternatively any other algorithms can be implemented, and/or the tactile outputs can be otherwise determined.

S200 can additionally or alternatively include determining any other outputs (e.g., visual), and/or any other processes.

Figure 10:
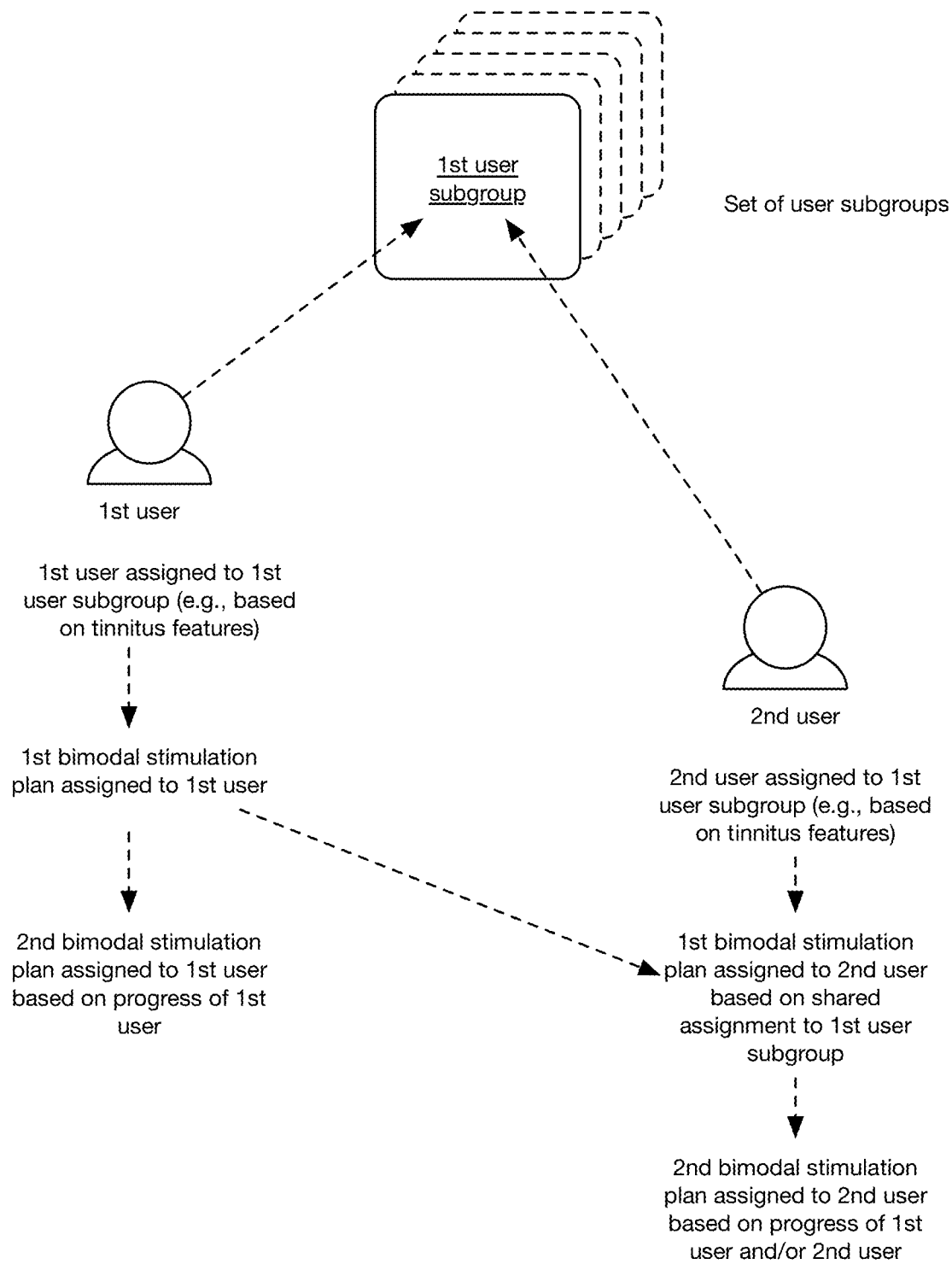
FIG. 10 depicts a schematic variation of determining a multimodal stimulation plan for a set of users.

S200 can optionally include assigning the user to a user subgroup based on the set of inputs (e.g., as shown in FIG. 10), which can be used to determine any or all of the sets of outputs described above. This can function, for instance, to leverage the learnings associated with a first user to guide the creation and/or selection of a multimodal stimulation plan for a second user. The user is preferably assigned to the subgroup based on features associated with the user's tinnitus (e.g., frequency, loudness, occurrence, etc.), but can additionally or alternatively be determined based on other shared features (e.g., demographic information, medical history, goals, etc.). Alternatively, S200 can be performed in absence of assigning the user to a subgroup.

In a first variation, S200 includes determining a $1^{st}$ set of audio outputs based on a predetermined toned based therapy (e.g., applied at a user device based on a tone-based therapy client application executing on the user device, applied at the tactile device, etc.), and determining a 2nd set of tactile outputs based on the $1^{st}$ set of audio outputs, wherein the tactile outputs are provided contemporaneously with the $1^{st}$ set of outputs. In specific examples, a location of each of the tactile outputs is determined based on a frequency value of a corresponding pure tone audio output and optionally produced through one or more illusion-based tactile effects.

In a first set of specific examples, the set of audio outputs includes a set of tones and/or partial tones which are played in a randomized order and with a set of randomized delays between adjacent audio outputs.

In a second set of specific examples, the set of audio outputs includes a set of tones and/or partial tones which are played in a particular order and with a set of randomized delays between adjacent audio outputs.

In a third set of specific examples, the set of audio outputs includes a set of tones and/or partial tones which are played in a particular and with a set of uniform delays between adjacent audio outputs.

Additionally or alternatively, non-tonal outputs can be provided as audio outputs.

In a second variation, a set of tactile outputs are provided in response to detecting audio in an environment of the user and with a set of one or more algorithms. In specific examples, a location of each of the tactile outputs is determined based on one or more frequency values associated with the audio in the environment of the user.

In a third variation, a set of tactile outputs are provided in response to music played for and/or by the user, wherein the tactile outputs can be predetermined based on known music, dynamically determined (e.g., with a set of one or more algorithms as described for detecting environmental audio, etc.), and/or any combination. In specific examples, a location of each of the tactile outputs is determined based on one or more frequency values associated with the music.

4.3 Method—Providing the Set of Outputs S300

The method 200 includes providing the set of outputs (equivalently referred to herein as the multimodal stimulation plan) S300, which functions to provide the multimodal stimulation to the user in accordance with any or all of the outputs determined in S200.

S300 is preferably performed in response to S200, but can additionally or alternatively be performed in response to S100 and/or at any other suitable times.

The set of outputs are preferably provided at least partially at the tactile device, but can additionally or alternatively be provided at any or all of: a user device, another supplementary device, naturally/organically provided in an environment of the user, and/or provided elsewhere.

In a first set of variations, the set of audio outputs are played at a speaker of a user device in communication with a tactile stimulation device, and the set of tactile outputs are provided contemporaneously with a set of actuators onboard the tactile stimulation device. The tactile outputs are preferably determined at a processing system at least partially onboard the user device (e.g., fully onboard the user device, in communication with a remote computing system, etc.) and transmitted (e.g., via a Bluetooth connection, via a WiFi connection, via a radio frequency connection, etc.) to the tactile stimulation device, but can additionally or alternatively be determined fully at another device and/or computing system (e.g., cloud-based computing system), at the tactile stimulation device, and/or at any other devices and/or combination of devices.

In a second set of variations, no audio outputs are played for the user (but rather occur naturally in the user's environment), wherein audio from the environment of the user is received at a microphone of the system (e.g., onboard the user device, onboard the tactile stimulation device, etc.) and processed to determine a set of tactile outputs to be provided with actuators of the tactile stimulation device.

4.4 Method—Adjusting any or all of the Set of Outputs S400

The method 200 can optionally include adjusting any or all of the set of outputs S400, which functions to adapt the bimodal stimulation plan to be optimal for the user and his or her evolving tinnitus condition. Additionally or alternatively, S400 can function to adapt the bimodal stimulation plan of a second user based on a detected progress of a first user (e.g., who experience the same type/frequency of tinnitus as the second user).

S400 is preferably performed in response to the set of outputs provided in S300 and further preferably in response to receiving a set of inputs in a second iteration of S100, but can additionally or alternatively be performed in response only to S300, in response to another process of the method 200, multiple times, and/or at any other times. Further additionally or alternatively, S400 can be performed in accordance with a predetermined schedule for the user and/or at any other times.

In some variations, for instance, a progress metric is determined based on one or more inputs from the user, such as a change in one or more features (e.g., frequency, loudness, daily occurrence, severity, etc.) associated with the user's tinnitus. In a set of specific examples, an input from the user might indicate that his or her tinnitus has decreased in loudness over time (e.g., with bimodal stimulation therapy), which can trigger an adjustment of the multimodal stimulation therapy based on this improvement. This can include, for instance, decreasing a total duration of the multimodal stimulation plan, decreasing a recommended frequency at which the user performs the multimodal stimulation plan, and/or otherwise adjusting the bimodal stimulation plan. In another set of specific examples, an input from the user might indicate that his or her tinnitus has changed in frequency, which can trigger a change in the frequency values of the audio outputs (and optionally subsequently the tactile outputs) provided to the user. Additionally or alternatively, the multimodal stimulation plan can be adjusted based on other information, based on multimodal stimulation plans of other users (e.g., with similar tinnitus frequency values), based on a schedule, randomly, and/or based on any other information.

Figure 6:
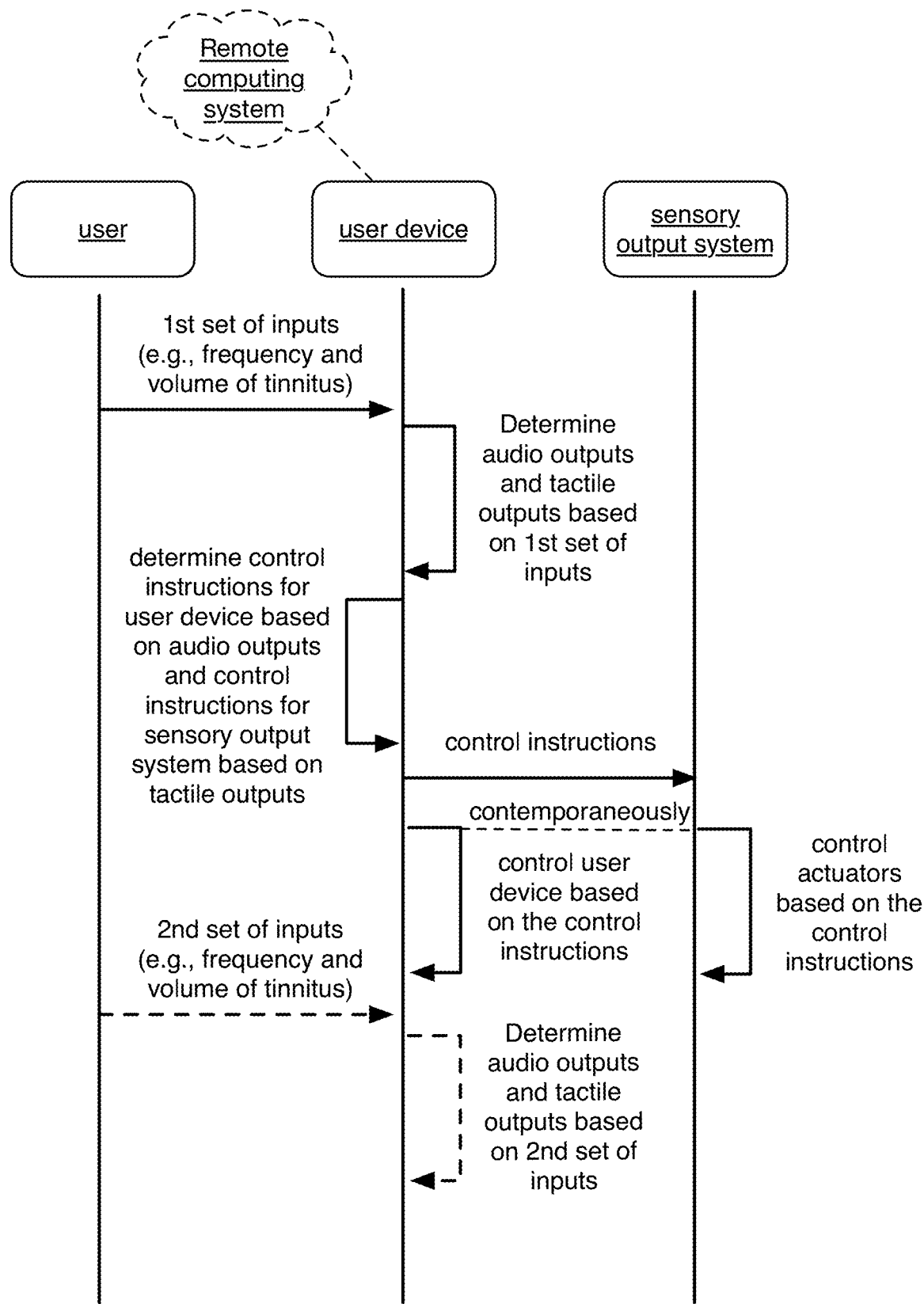
FIG. 6 depicts a schematic variation of information exchanged between different components of a system for multimodal stimulation.
Figure 7:
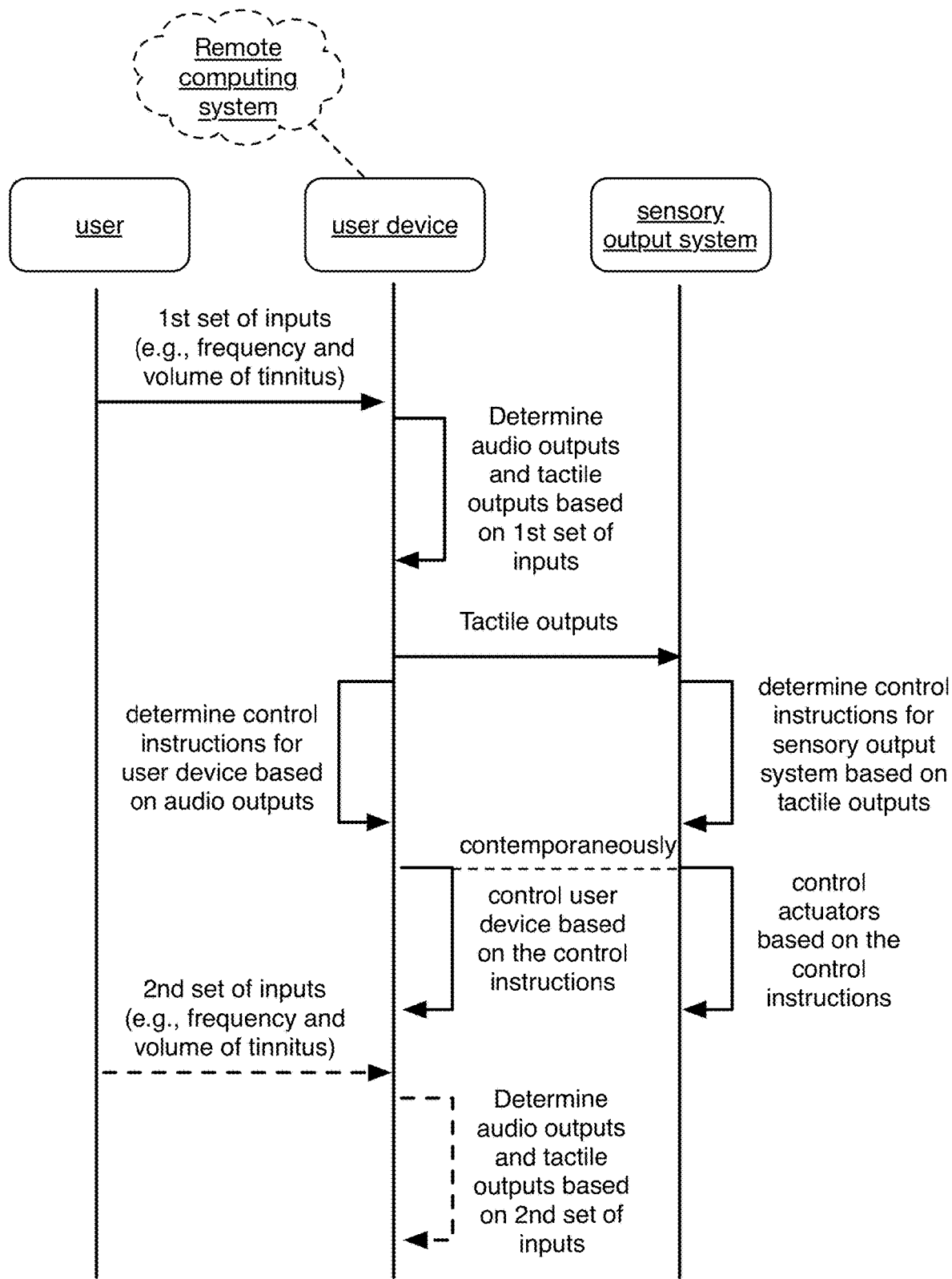
FIG. 7 depicts a schematic variation of information exchanged between different components of a system for multimodal stimulation.
Figure 8:
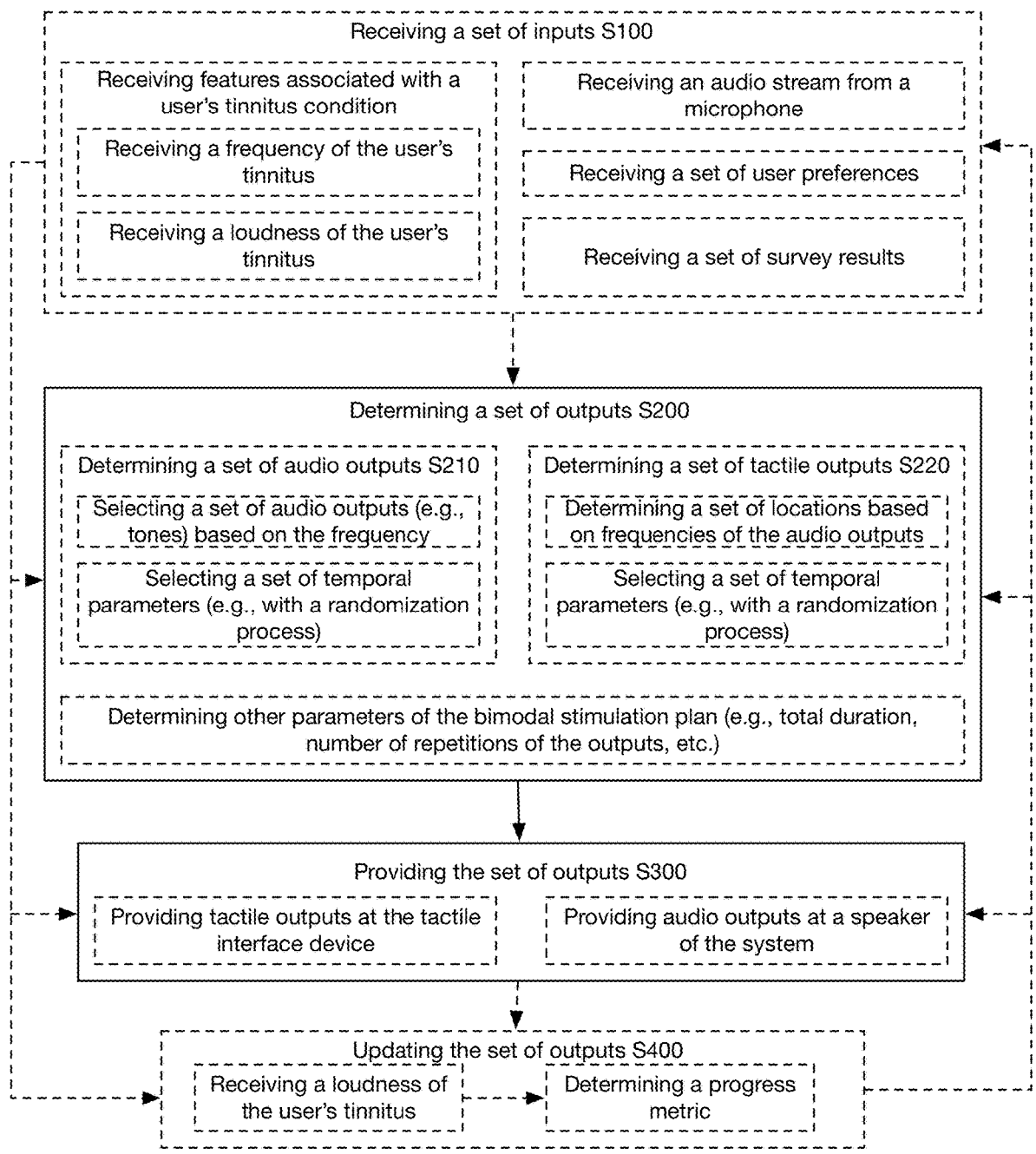
FIG. 8 depicts a schematic of a variation of a method for multimodal stimulation.

Variations depicting the updating of a multimodal stimulation plan for user are shown in FIG. 6 and FIG. 7.

Additionally or alternatively, S400 can include any other processes.

4.5 Method—Variations

In a first variation of the method 200, the method 200 implements a tone-based therapy for users experiencing tinnitus, wherein in the tone-based therapy, the user wears a haptic stimulation device (e.g., haptic stimulation wristband device) while listening to a series of short tones (e.g., with a speaker of a user device, with a set of headphones, with a speaker onboard the haptic stimulation device, etc.), which vary in frequency. The tones can be of a variety of durations and frequencies and can have a variety of silence between each.

In a specific example, the set of audio outputs are selected based on a user's tinnitus frequency (e.g., as input at a client application) and include: a first set of tonal sounds (e.g., pure tones, sine tones, complex tones, etc.) which have frequency values below the user's tinnitus frequency; a second set of tonal sounds (e.g., next octave of tones) which have frequency values above the user's tinnitus frequency; and optionally one or more sounds (e.g., tonal sound) at the user's tinnitus frequency. The frequency values of the audio outputs are preferably nonlinearly spaced (e.g., logarithmically spaced), but can additionally or alternatively include linear spacings, semitone spacings, and/or any other spacings. The set of audio outputs are preferably played to the user in a randomized fashion and if the set of audio outputs are repeated, each repeat is preferably played in a randomized fashion and without replacement (without repeating an identical output before all other outputs in the set have been played once), but the audio outputs can alternatively be played in an ordered fashion (e.g., increasing frequency, decreasing frequency, increasing then decreasing frequency, etc.), with replacement, and/or in any other ways. The set of audio outputs are preferably played with a variable time delay between sequential audio outputs, where the variable time delay is determined in a randomized fashion, but the audio outputs can alternatively be played with fixed time delays, with predetermined variable time delays, without time delays, and/or in any other fashion. A set of tactile outputs are preferably played contemporaneously with (e.g., simultaneously with, overlapping with, in quick succession, within 1 ms, within 5 ms, within between 1 and 100 ms, etc.) the set of audio outputs in a 1:1 fashion, where the frequency of each audio output is used to determine the location of the tactile output (e.g., through the selection of the amplitudes for the set of actuators), which is produced based on the actuation of one or more of a set of actuators onboard the tactile stimulation device. The bimodal stimulation plan, which refers to the playing of the audio outputs and the tactile outputs, can optionally be played for a particular time period (e.g., 10 minutes, less than 10 minutes, greater than 10 minutes, etc.) daily to the user (and/or at any other suitable schedule such as every other day, once a week, multiple times per day, one or more times per week, one or more times per month, based on a trigger, based on a user preference, etc.).

In another specific example (e.g., as shown in FIGS. 9A-9D), a set of tones (e.g., 20 pure tones) and/or partial tones which vary in a logarithmic scale from 500 Hz to 8000 Hz (e.g., 500 Hz, 578 Hz, 669 Hz, 774 Hz, 896 Hz, 1037 Hz, 1200 Hz, 1388 Hz, 1606 Hz, 1859 Hz, 2151 Hz, 2489 Hz, 2880 Hz, 3333 Hz, 3856 Hz, 4462 Hz, 5163 Hz, 5975 Hz, 6913 Hz, and 8000 Hz) are played forward and then backward, with each tone lasting for a predetermined duration (e.g., 425 ms, less than 425 ms, greater than 425 ms, etc.) and containing a duration of silence (e.g., 200 ms, less than 200 ms, greater than 200 ms, etc.) before the following tone. This train/sequence of tones and/or any other tones (random frequencies, constant frequencies, linearly spaced, other durations or varying durations of audio and/or silence, etc.) can be played for a time period (e.g., 10 minutes, less than 10 minutes, greater than 10 minutes, etc.) daily to the user (and/or at any other suitable schedule such as every other day, once a week, multiple times per day, one or more times per week, one or more times per month, based on a trigger, based on a user preference, etc.). One or more algorithms for the tactile outputs can optionally be run offline and then played back with a slight advance, such that the vibrations occur some time (e.g. 50 ms, greater than 50 ms, shorter than 50 ms, etc.) before the corresponding audio. Additionally or alternatively, the tone-based therapy can be otherwise implemented and/or include any other processes.

Additionally or alternatively, any other outputs can be provide to the user in any suitable fashion.

In a second variation of the method 200, which can be implemented additional or alternative to those described above, the method 200 implements an organic exposure therapy for users experiencing tinnitus, wherein in the organic exposure therapy, the user wears a haptic stimulation device (e.g., haptic stimulation wristband device) throughout his or her day and is exposed to any sounds they are normally exposed to. Through feeling the vibrations from the wristband while contemporaneously and/or in quick succession (e.g., within 10 ms, within between 1 and 500 ms, within between 1 and 100 ms, etc.) hearing the audio (e.g., whether from tone-based therapy, from the organic exposure therapy, or both), the user can experience a decrease in tinnitus symptoms. One or more algorithms can optionally be implemented to play vibrations with a delay, such that they occur some time (e.g. 50 ms, greater than 50 ms, shorter than 50 ms, etc.) after the corresponding audio occurred.

In a third variation of the method 200, which can be implemented additional or alternative to those described above, the method 200 plays music to the user through one or more speakers while contemporaneously providing corresponding tactile outputs (e.g., based on the frequencies in the music).

Although omitted for conciseness, the preferred embodiments include every combination and permutation of the various system components and the various method processes, wherein the method processes can be performed in any suitable order, sequentially or concurrently.

Embodiments of the system and/or method can include every combination and permutation of the various system components and the various method processes, wherein one or more instances of the method and/or processes described herein can be performed asynchronously (e.g., sequentially), contemporaneously (e.g., concurrently, in parallel, etc.), or in any other suitable order by and/or using one or more instances of the systems, elements, and/or entities described herein. Components and/or processes of the following system and/or method can be used with, in addition to, in lieu of, or otherwise integrated with all or a portion of the systems and/or methods disclosed in the applications mentioned above, each of which are incorporated in their entirety by this reference.

As a person skilled in the art will recognize from the previous detailed description and from the figures and claims, modifications and changes can be made to the preferred embodiments of the invention without departing from the scope of this invention defined in the following claims.

We claim:

1. A method for providing a bimodal tinnitus therapy to a user, the method comprising:
   at a speaker, providing a set of audio stimuli, wherein audio stimuli of the set are provided in an ordered sequence, wherein:
      the ordered sequence is determined with a first randomization process; and
      each of the set of audio stimuli is provided before replacement, wherein additional instances of providing the set of audio stimuli are determined with a second randomization process;
   contemporaneously with providing the set of audio stimuli, providing a set of vibratory stimuli at a set of actuators arranged onboard a tactile stimulation device, wherein vibratory stimuli of the set are provided in accordance with:
      a set of time delays occurring between adjacent vibratory stimuli of the set of vibratory stimuli, wherein each time delay defines a gap between an end of a vibratory stimulus and a beginning of a subsequent vibratory stimulus, wherein duration values of the set of time delays are determined with a third randomization process; and
      a set of locations;
   and initiating the bimodal tinnitus therapy at the tactile stimulation device.

2. The method of claim 1, further comprising receiving a first feature associated with a tinnitus condition of the user, wherein the set of audio stimuli are determined based on the first feature.

3. The method of claim 2, further comprising:
   receiving a second feature associated with the tinnitus condition of the user;
   updating the set of audio stimuli based on the second feature;
   providing the updated set of audio stimuli contemporaneously with the set of vibratory stimuli.

4. The method of claim 2, further comprising assigning the user to a subgroup based on the first feature, wherein the set of audio stimuli and the set of vibratory stimuli are determined based on the subgroup.

5. The method of claim 2, wherein the set of audio stimuli are determined based on a loudness value associated with the tinnitus condition of the user.

6. The method of claim 1, wherein the tactile stimulation device is worn on a body region of the user, wherein the body region comprises at least one of: a hand, a wrist, an arm, a finger, a leg, a torso, a neck, a head, or an ankle.

7. The method of claim 1, wherein the set of audio stimuli are determined based on a tinnitus frequency value provided by the user, wherein the set of audio stimuli comprises a set of octaves of tones, wherein the set of octaves of tones comprises an octave of tones below the tinnitus frequency value provided by the user and an octave of tones above the tinnitus frequency value provided by the user.

8. The method of claim 1, wherein the set of actuators are in contact with the user, wherein the set of locations comprises a location arranged between two or more actuators of the set of actuators.

9. The method of claim 1, further comprising contemporaneously providing the set of audio stimuli and the set of vibratory stimuli to the user in repeated sessions, wherein the repeated sessions span a duration of 10 minutes.

10. The method of claim 1, wherein the set of actuators comprises four independently controllable vibratory motors.

11. A system for providing bimodal tinnitus therapy to a user, the system comprising:
   a wearable device, wherein the wearable device comprises a set of actuators;
   a processing system configured to:
      determine a bimodal stimulation plan for the user based on a first feature associated with a tinnitus condition of the user, wherein the bimodal stimulation plan comprises:
         a set of audio outputs to be conveyed by a speaker, the set of audio outputs provided contemporaneously with a set of tactile outputs, the set of tactile outputs to be conveyed at the set of actuators, wherein the set of audio outputs is defined based on a set of audio parameters comprising:
            a set of sounds; and
      an ordered sequence of the set of sounds, wherein the ordered sequence is determined with a first randomization process, wherein each of the set of audio stimuli is provided before replacement, wherein additional instances of providing the set of audio stimuli are determined with a second randomization process;
         a set of parameters of vibration comprising a set of time delays, wherein the set of tactile outputs is defined based on the set of parameters of vibration, wherein each time delay defines a gap between an end of a tactile output and a beginning of a subsequent tactile output, wherein duration values of the set of time delays are determined with a third randomization process; and
      implementing the bimodal stimulation plan at the wearable device.

12. The system of claim 11, wherein the set of parameters of vibration comprises a set of actuation intensities for the set of actuators, the set of actuation intensities configured to produce tactile sensation at a set of locations.

13. The system of claim 11, wherein the wearable device is configured to be worn on a body region of the user, wherein the body region comprises at least one of: a hand, a wrist, an arm, a finger, a leg, a torso, a neck, a head, or an ankle.

14. The system of claim 11, wherein the set of actuators are collectively configured to produce tactile sensation at a set of locations, wherein the set of locations comprise a continuous range of locations including and between locations of the set of actuators.

15. The system of claim 11, wherein the processing system is partially arranged onboard the wearable device.

16. The system of claim 11, wherein the processing system is further configured to compare a second feature associated with the tinnitus condition of the user with the first feature associated with the tinnitus condition of the user, and determine an updated bimodal stimulation plan for the user based on the comparison.

17. The system of claim 11, wherein the first feature comprises a tinnitus frequency value, wherein the set of sounds is centered on a nonlinear scale around the tinnitus frequency value.

18. The system of claim 11, wherein the bimodal stimulation plan further comprises a set of locations, wherein each of the set of locations is a single location, wherein at least a portion of the set of locations is produced based on a contemporaneous actuation of multiple actuators of the set of actuators.

19. The system of claim 11, wherein the bimodal stimulation plan further comprises a set of locations, wherein the set of locations is determined based on the first feature and a predetermined mapping.

20. The system of claim 11, wherein the first feature comprises a tinnitus frequency value, wherein the set of sounds comprises a set of octaves of tones below the tinnitus frequency value and a set of octaves of tones above the tinnitus frequency value.

* * * * *